US008095389B2

(12) United States Patent
Dalton et al.

(10) Patent No.: US 8,095,389 B2
(45) Date of Patent: Jan. 10, 2012

(54) COMPUTER SYSTEMS AND METHODS FOR SELECTING SUBJECTS FOR CLINICAL TRIALS

(75) Inventors: William S. Dalton, Temple Terrace, FL (US); Timothy Yeatman, Thonotasassa, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 712 days.

(21) Appl. No.: 11/879,387

(22) Filed: Jul. 16, 2007

(65) Prior Publication Data

US 2008/0033658 A1  Feb. 7, 2008

Related U.S. Application Data

(60) Provisional application No. 60/831,560, filed on Jul. 17, 2006.

(51) Int. Cl.
G06Q 50/00 (2006.01)
C12Q 1/68 (2006.01)
(52) U.S. Cl. .................................. 705/3; 705/2; 435/6
(58) Field of Classification Search .................. 705/2–4
See application file for complete search history.

(56) References Cited

U.S. PATENT DOCUMENTS

| 6,528,260 | B1* | 3/2003 | Blumenfeld et al. | 435/6 |
|---|---|---|---|---|
| 6,960,439 | B2* | 11/2005 | Bevilacqua et al. | 435/6 |
| 7,332,272 | B1* | 2/2008 | Gunther | 435/6 |
| 2002/0046054 | A1* | 4/2002 | Morand et al. | 705/1 |
| 2002/0051978 | A1* | 5/2002 | Roth et al. | 435/6 |
| 2002/0155422 | A1* | 10/2002 | Ingber et al. | 435/4 |
| 2003/0229455 | A1* | 12/2003 | Bevilacqua et al. | 702/20 |
| 2003/0233197 | A1* | 12/2003 | Padilla et al. | 702/20 |
| 2004/0093240 | A1 | 5/2004 | Shah | |
| 2004/0133352 | A1 | 7/2004 | Bevilacqua et al. | |
| 2004/0225449 | A1* | 11/2004 | Bevilacqua et al. | 702/20 |
| 2005/0256745 | A1 | 11/2005 | Dalton | |

(Continued)

FOREIGN PATENT DOCUMENTS

WO    WO 03/039234    5/2003

(Continued)

OTHER PUBLICATIONS

Identifying—definition as taken from Google definitions Apr. 7, 2010.*

(Continued)

*Primary Examiner* — Neal Sereboff

(74) *Attorney, Agent, or Firm* — Fish & Richardson P.C.

(57) ABSTRACT

Computers, computer program products, and methods for identifying a plurality of subjects for a clinical trial are provided. A candidate set of molecular profiles in a stored plurality of molecular profiles are identified. Each such profile has measurements for a discriminating set of cellular constituents that match the measurements of corresponding cellular constituents in a responder set of biological samples, thereby identifying the plurality of subjects for the trial from those subjects from which the candidate set of molecular profiles were derived. Each respective molecular profile in the stored plurality of profiles has measurements of a plurality of cellular constituents from a respective biological sample in a plurality of samples obtained from a first plurality of subjects. The discriminating set of cellular constituents is identified from those cellular constituents in the plurality of cellular constituents whose measurement values discriminates between the responder and nonresponder sets of biological samples.

48 Claims, 14 Drawing Sheets

U.S. PATENT DOCUMENTS

| | | |
|---|---|---|
| 2006/0029944 A1* | 2/2006 | Huang et al. ............ 435/6 |
| 2006/0195269 A1 | 8/2006 | Yeatman et al. |
| 2006/0281134 A1* | 12/2006 | Love ............ 435/7.1 |

FOREIGN PATENT DOCUMENTS

| | | |
|---|---|---|
| WO | WO 2005/116890 | 12/2005 |
| WO | WO 2006/002415 | 1/2006 |
| WO | WO 2006/044017 | 4/2006 |
| WO | WO 2006/084272 A2 | 8/2006 |

OTHER PUBLICATIONS

Identifying—definition as taken from dictionary.com Apr. 7, 2010.*

Abrams, "Adjuvant Therapy for Breast Cancer—Results From The USA Consensus Conference," *Breast Cancer*, 2001, 8(4):298-304.

Alvarado et al., "The Potential Role of Gene Expression in the Management of Primary and Metastatic Colorectal Cancer," *Cancer Control.*, 2006, 13(1):27-31.

Carr et al., "Genomic and Proteomic Approaches for Studying Human Cancer: Prospects for True Patient-Tailored Therapy," *Hum. Genomics.*, 2004, 1(2):134-140.

Dalton et al., "Cancer Biomarkers—An Invitation to the Table," *Science*, 2006, 312(5777):1165-1168.

Jensen et al., "Microarrays in Gastrointestinal Cancer: Is Personalized Prediction of Response to Chemotherapy at Hand?" *Curr. Opin. Oncol.*, 2006, 18(4):374-380.

Morrow et al., "Who Should Not Receive Chemotherapy? Data From American Databases and Trials," *J. Natl. Cancer. Inst. Monogr.*, 2001, (30):109-113.

Raetz et al., "Impact of Microarray Technology in Clinical Oncology," *Cancer Invest.*, 2004, 22(2):312-320.

Srivastava, "Molecular Screening of Cancer: The Future is Here," *Mol. Diagn. Ther.*, 2006, 10(4):221-230.

Yeatman, "The Future of Clinical Cancer Management: One Tumor, One Chip," *Am. Surg.*, 2003, 69(1):41-44.

Yeatman, "Carcinoembryonic Antigen, Biomarker Discovery, and Trial Design," *Ann. Surg. Oncol.*, 2006, 13(5):600-601.

ISA/US International Search Report, dated Jul. 8, 2008, for International Application No. PCT/US2007/016239.

Barrett et al., "Treatment of the Common Cold with Unrefined Echinacea," Annals of Internal Medicine, 2002, vol. 137(12):939-946.

Feng et al., "Transcriptional Profile of Mechanically Induced Genes in Human Vascular Smooth Muscle Cells," Circ. Res., 1999, vol. 85:1118-1123.

Supplementary European Search Report in EP 07 810 552.5, mailed Dec. 9, 2010, 9 pages.

* cited by examiner

| CLINICAL FEATURE | | ~52-x |
|---|---|---|
| | ICD-9 CODE FOR CLINICAL FEATURE | ~302-1 |
| | DATE CLINICAL CHARACTERIZATION WAS MADE | ~304-1 |
| | ⋮ | |

FIG.3

| DEMOGRAPHIC CHARACTERIZATION | ~60-x |
|---|---|
| GENDER | ~402-x |
| MARITAL STATUS | ~404-x |
| ETHNICITY | ~406-x |
| LANGUAGE | ~408-x |
| EYE COLOR | ~410-x |
| HAIR COLOR | ~412-x |
| HEIGHT | ~414-x |
| WEIGHT | ~416-x |
| SOCIAL SECURITY NUMBER | ~418-x |
| NAME | ~420-x |
| DAYE OF BIRTH/AGE | ~422-x |
| EDUCATION STATUS | ~424-x |
| PRIMARY PHYSICIAN | ~426-x |
| REFERRING PHYSICIAN | ~428-x |
| REFERRAL SOURCE | ~430-x |
| PATIENT DISABILITIES | ~432-x |
| INDICATION AS TO WHETHER PATIENT IS A SMOKER | ~434-x |
| INDICATION AS TO WHETHER PATIENT CONSUMES ALCOHOL | ~436-x |
| RESIDENTIAL ADDRESS OF PATIENT | ~438-x |
| PATIENT TELEPHONE ADDRESS | ~440-x |
| INSURANCE CARRIER FOR A PATIENT INSURANCE POLICY | ~442-x |
| MEMBER INDENTIFIER NUMBER FOR INSURANCE POLICY | ~444-x |
| ⋮ | |

FIG.4

QUESTIONS FOR SURGEON

- AWOD? AWD?
- FOLLOWING PRIMARY SURGERY:
  - DATE OF PRIMARY SURGERY: MO/YR
  - DID THE PATIENT RECEIVE MORE THAN 3 MO OF ADJUVANT CHEMOTHERAPY? Y/N
    - IF Y, WHAT DRUGS USED
      - COLON
        - \>\> 5FU
        - \>\> LV
        - \>\> OXALIPLATIN
        - \>\> XELODA
        - \>\> IRINOTECAN
  - HAS THERE BEEN A RECURRENCE SINCE SURGERY? Y/N
    - IF Y, LOCAL/DISTANT
    - IF Y, DATE OF RECURRENCE

FIG.5

QUESTIONS FOR MED ONC

- AWOD? AWD?
- DOES THE PATIENT HAVE METASTATIC DISEASE? Y/N
- IF Y, IS THE PATIENT CURRENTLY RECEIVING SYSTEMIC THERAPY? Y/N
- IF Y, FIRST/SECOND REGIMEN?
- IF Y, WHAT IS THE REGIMEN OF DRUGS
  - COLON
    - 5FU
    - LV
    - OXALIPLATIN
    - IRINOTECAN
    - AVASTIN
    - ERBITUX
- IF Y, HAS THERE BEEN A RESPONSE TO THERAPY BY RECIST CRITERIA? Y/N
- OR ... HAS THE PATIENT PROGRESSED ON THERAPY REQUIRING A SECOND REGIMEN? Y/N

FIG.6

DATE OF CLINIC VISIT: ___/___/___

---
METASTATIC PATIENT F/U
---

NOTE: ALL QUESTIONS SHOULD BE APPLICABLE TO THE 12 MO PREVIOUS TO THE CLINIC DATE ABOVE

1. CURRENT DISEASE STATUS:
   ○ AWOD
   ○ AWD

2. EVIDENCE OF METASTASIS?
   ○ YES  IF YES, DOCUMENTED BY:
   ○ NO   ○ CT/MRI/US
          ○ PET
          ○ BIOPSY

3. IS PATIENT CURRENTLY RECEIVING CHEMOTHERAPY?
   ○ YES  IF YES, CHOOSE DRUGS: (DROP DOWN LIST)
   ○ NO      >COLON CANCER
             >LUNG CANCER
             >BREAST CANCER

COLON CANCER:
   ○ 5FU
   ○ LV
   ○ OXALIPLATIN
   ○ IRINOTECAN
   ○ BEVICUZIMAB
   ○ CAPECITABINE
   ○ CETUXIMAB

LUNG CANCER:
   ○ CARBOPLATIN
   ○ TAXOL
   ○ GEMCITABINE
   ○ IRESSA

4. HAS THE PATIENT PROGRESSED ON THERAPY?
   ○ YES
   ○ NO

FIG.7A

DATE OF CLINIC VISIT: ___/___/___

PRIMARY RESECTION F/U
NOTE: ALL QUESTIONS SHOULD BE APPLICABLE TO THE 12 MO PREVIOUS TO THE CLINIC DATE ABOVE

1. CURRENT DISEASE STATUS:
   ○ NED
   ○ AWD

2. DID THE PATIENT RECEIVE PRE-OPERATIVE CHEMOTHERAPY?
   ○ YES
   ○ NO

3. HAS THE PATIENT RECEIVED OR IS PATIENT CURRENTLY RECEIVING "ADJUVANT" CHEMOTHERAPY?
   ○ YES  IF YES, CHOOSE DRUGS: (DROP DOWN LIST)
   ○ NO       >COLON CANCER
              >LUNG CANCER
              >BREAST CANCER

COLON CANCER:
   ○ 5FU
   ○ LV
   ○ OXALIPLATIN
   ○ IRINOTECAN
   ○ BEVICUZIMAB
   ○ CAPECITABINE
   ○ CETUXIMAB

4. EVIDENCE OF RECURRENCE?
   ○ YES  IF YES, DOCUMENTED BY:
   ○ NO    ○ CT/MRI/US
           ○ PET
           ○ BIOPSY

IF YES,
   ○ LOCAL/REGIONAL
   ○ DISTANT

FIG.7B

| MOLECULAR PROFILE OF SUBJECT BASED ON BIOLOGICAL SPECIMEN FROM SUBJECT 1 | ~ 610-1 |
|---|---|
| IDENTITY OF CELLULAR CONSTITUENT 1 | ~ 802-1 |
| ABUNDANCE LEVEL OF CELLULAR CONSTITUENT 1 AT TIME POINT 1 | ~ 804-1-1 |
| ABUNDANCE LEVEL OF CELLULAR CONSTITUENT 1 AT TIME POINT 2 | ~ 804-1-2 |
| ... | |
| ABUNDANCE LEVEL OF CELLULAR CONSTITUENT 1 AT TIME POINT N | ~ 804-1-N |
| IDENTITY OF CELLULAR CONSTITUENT 2 | ~ 802-2 |
| ABUNDANCE LEVEL OF CELLULAR CONSTITUENT 2 AT TIME POINT 1 | ~ 804-2-1 |
| ABUNDANCE LEVEL OF CELLULAR CONSTITUENT 2 AT TIME POINT 2 | ~ 804-2-2 |
| ... | |
| ABUNDANCE LEVEL OF CELLULAR CONSTITUENT 2 AT TIME POINT N | ~ 804-2-N |
| ... | |
| IDENTITY OF CELLULAR CONSTITUENT Y | ~ 802-Y |
| ABUNDANCE LEVEL OF CELLULAR CONSTITUENT Y AT TIME POINT 1 | ~ 804-Y-1 |
| ABUNDANCE LEVEL OF CELLULAR CONSTITUENT Y AT TIME POINT 2 | ~ 804-Y-2 |
| ... | |
| ABUNDANCE LEVEL OF CELLULAR CONSTITUENT Y AT TIME POINT N | ~ 804-Y-N |

FIG.8

MEDIKIOSK
DALVANON

TCC MODULES – PAST MEDICAL HISTORY MODULE          CANCEL CHECK-IN

PLEASE COMPLETE THE FOLLOWING FORM AND TOUCH "NEXT SCREEN" WHEN COMPLETE.

HAVE YOU EVER HAD A SURGERY?
○ YES
○ NO

HAVE YOU EVER BEEN HOSPITALIZED (OTHER THAN DURING CHILDBIRTH)?
○ YES
○ NO

DID A DOCTOR EVER SAY THAT YOU HAVE ANY OF THE FOLLOWING INFECTIONS (MARK ALL THAT APPLY)?
☐ AIDS/HIV     ☐ HEPATITIS B     ☐ OTHER, PLEASE SPECIFY: [ENTER INFECTION HERE]
☐ HEPATITIS C                     ○ NO, I HAVE NONE OF THESE PROBLEMS
                                  ○ I NEED HELP ANSWERING QUESTION

| @ | Q | W | E | R | T | Y | U | I | O | P | 1 | 2 | 3 | 4 |
| CAPS | A | S | D | F | G | H | J | K | L | / | 5 | 6 | 7 | 8 |
| Z | X | C | V | B | N | M | . | SPACE | BACK SPACE | SYMBOLS | 9 | 0 |

NEXT SCREEN

FIG.9A ically dominated time to market, has undergone a
COMPUTER SYSTEMS AND METHODS FOR SELECTING SUBJECTS FOR CLINICAL TRIALS This application claims the benefit under 35 U.S.C. §119 (e) of U.S. Provisional Application No. 60/831,560, filed Jul. 17, 2006, which is incorporated herein by reference in its entirety.

1. FIELD OF THE INVENTION

The field of this invention relates to computer systems and methods for selecting subjects for clinical trials.

2. BACKGROUND OF THE INVENTION

A number of factors drive the period of time and cost required for new drug development. The discovery process, which formerly dominated time to market, has undergone a revolution due to techniques such as combinatorial chemistry and high throughput screening. The regulatory phase, which also previously lengthened drug development and marketing, has been reduced due to FDA reforms and European Union harmonization. Currently, human clinical trials have become the main bottleneck in getting a drug to market. It is estimated that the time required for clinical trials is roughly fifty percent (or 7.5 years) of the 15 years often required for the average new drug to come to market.

In U.S. pharmaceutical companies, a large percentage of total annual pharmaceutical research and development funds is spent on human clinical trials. Spending on clinical trials is growing at approximately fifteen percent per year, almost fifty percent above the industry's sales growth rate. Trials are growing both in number and complexity. For example, the average new drug submission to the U.S. Food and Drug Administration (FDA) now contains more than double the number of clinical trials, more than triple the number of patients, and more than a fifty percent increase in the number of procedures per trial, since the early 1980s.

One difficulty with conducting clinical trials is the selection of suitable subjects for the clinical trial. Not all subjects that have a particular disease will respond to a given therapy. For example, for every 100 node-negative breast cancer patients only a small fraction of patients are likely to benefit from the relatively toxic regimen. See Morrow and Krontiras, 2001, *J. Natl. Cancer Inst. Monogr.* 30:109-113; and Abrams, 2001, *Breast Cancer* 8:298-304. Similarly, for every 100 node-negative patients undergoing a Whipple procedure for pancreatic cancer at best only 20 survive 5 years or longer. See Yeo and Cameron, 1999, *Curr. Probl. Surg.* 36:59-152. Thus, failure to make rational clinical trial enrollment decisions can cause a clinical trial to fail for a given therapy, even in instances where the therapy has, in fact, significant efficacy in some populations.

To ensure the success of such clinical trials, what is needed in the art are systems and methods for identifying subjects that are suitable for clinical trials.

3. SUMMARY OF THE INVENTION

One aspect of the present invention provides a method of identifying a plurality of subjects for a clinical trial for a therapy of interest. In the method, a candidate set of molecular profiles, in a stored first plurality of molecular profiles, is identified. Each molecular profile in the candidate set of molecular profiles has measurements for a discriminating set of cellular constituents that match the measurements of the discriminating set of cellular constituents in a responder set of biological samples. In this way the plurality of subjects for the clinical trial are identified from those subjects from which the candidate set of molecular profiles were derived. Each respective molecular profile in the stored first plurality of molecular profiles comprises measurements of a first plurality of cellular constituents from a respective biological sample in a first plurality of biological samples obtained from a first plurality of subjects. The discriminating set of cellular constituents is identified from those cellular constituents in the first plurality of cellular constituents whose measurement values taken prior to exposure to the therapy of interest discriminates between the responder set of biological samples and a nonresponder set of biological samples.

In some embodiments, a molecular profile is measure for each biological sample in the first plurality of biological samples thereby obtaining the first plurality of molecular profiles. In some embodiments, the first plurality of molecular profiles are stored. In some embodiments, a molecular profile is measured for each biological sample in a second plurality of biological samples prior to exposure to the therapy of interest, thereby obtaining a second plurality of molecular profiles. Each biological sample in the second plurality of biological samples is from a subject having a disease of interest or is a model for the disease of interest and each respective molecular profile in the second plurality of molecular profiles comprises measurements of two or more of the first plurality of cellular constituents from a respective biological sample in the second plurality of biological samples. In such embodiments, the method further comprises identifying the responder set of biological samples that are responders to the therapy of interest for the disease of interest in the second plurality of biological samples and a nonresponder set of biological samples that are nonresponders to the therapy of interest for the disease of interest in the second plurality of biological samples. Each biological sample in the second plurality of biological samples can be, for example, a cell line. Each biological sample in the second plurality of biological samples can be, for example, obtained from a subject in a second plurality of subjects. In some instances, each biological sample in the second plurality of biological samples is a portion of a tumor. In some embodiments, the responder set of biological samples and the nonresponder set of biological samples is identified in the first plurality of biological samples.

In some embodiments, the method further comprises making a first observation of a clinical feature, other than a cellular constituent, in a subject in the plurality of subjects at a first time point and storing the first observation of the clinical feature with the molecular profile for the subject. In some embodiments, the molecular profile for the subject is in the candidate set of molecular profiles, the first observation is absence or presence of the clinical feature in the subject, and the method further comprises (i) removing the molecular profile from the candidate set when the clinical feature is absent from the subject, and (ii) retaining the molecular profile in the candidate set when the clinical feature is present in the subject. In some embodiments, the method further comprises (i) making a second observation of the clinical feature in the subject at a second time point and (ii) storing the second observation of the clinical feature with the molecular profile for the subject. In some embodiments, the second time point is at least one day, at least one week, or at least one year after the first time point. In some embodiments, the clinical feature is a disease such as arthritis, asthma, an allergy, cancer, chronic fatigue syndrome, diabetes, epilepsy, heart disease, hemochromatosis, hepatitis B, hepatitis C, osteoporosis, breast cancer, cervical cancer, colorectal cancer, lung cancer, oral cancer, ovarian cancer, prostate cancer, skin cancer, or testicular cancer. In some embodiments, the clinical feature is ankle swelling, anorexia, dyspnoea, fatigue, high blood pressure, hypoxemia, lethargy, lymphopenia, nocturnal cough, nocturnal dyspnoea, obesity, orthopnoea, paroxysmal, a viral infection, reduced exercise tolerance, tachycardia, tachypnea, or wheeze.

In some embodiments, the first plurality of cellular constituents comprises more one thousand cellular constituents, more than two thousand cellular constituents, more than three thousand cellular constituents, more than four thousand cellular constituents, more than five thousand cellular constituents, between three thousand and ten thousand cellular constituents, or less than twenty-five thousand cellular constituents. In some embodiments, the molecular profile for each biological sample in the first plurality of biological samples is obtained using a microarray that comprises oligonucleotides representing more than five thousand cellular constituents. In some embodiments, a cellular constituent in the discriminating set of cellular constituents is a nucleic acid or a protein. In some embodiments, measurements for a cellular constituent in the set of discriminating set of cellular constituents discriminates with a p value of less than 0.05 as determined by a parametric (e.g., analysis of variance, a t-test, etc.) or nonparametric test (e.g., Chi-square test, a Phi coefficient, a Fisher exact test, etc.) using measurements for the cellular constituent in the responder set of biological samples and measurements for the cellular constituent in the nonresponder set of biological samples.

In some embodiments, the therapy of interest is exposure to a drug, exposure to radiation, exposure to radio-frequency ablation, or exposure to an siRNA. In some embodiments, the first plurality of subjects are human, bovine (cow), porcine, canine, feline (cat), ovine (sheep), equine, lapine (rabbit), hamster, chicken, rat, mouse, chimpanzee, or baboon. In some embodiments, a subject is an animal, preferably a mammal, more preferably a non-human primate, and most preferably a human. The terms "subject," "individual," and "patient" are used interchangeably herein.

In some embodiments, the method further comprises obtaining patient information about a subject (e.g., an address where the subject lives, next of kin contact information, a telephone number for the subject, the age of the subject, an allergy that the subject has, a height of the subject, a weight of the subject, a race of the subject, insurance information for the subject, etc.) in the plurality of subjects and storing it with the molecular profile for the subject. In some embodiments this is done by directly entering the patient information into a web-based questionnaire. In some embodiments, the molecular profile for the subject is in the candidate set of molecular profiles and the method further comprises (i) removing the molecular profile from the candidate set when the patient information does not satisfy a selection criterion (e.g., a minimum or maximum age, a minimum or maximum weight, etc.) and (ii) retaining the molecular profile in the candidate set when the patient information satisfies the selection criterion.

In some aspects of the invention, the method further comprises subjecting the plurality of subjects to the therapy of interest and then identifying a first set of subjects in the plurality of subjects that are responders to the therapy of interest and a second set of subjects in the plurality of subjects that are not responders to the therapy of interest. Then, a revised set of discriminating cellular constituents is identified whose measurement values taken from the plurality of subjects prior to exposure to the therapy of interest discriminates between the first set of subjects in the plurality of subjects that are responders to the therapy of interest and the second set of subjects in the plurality of subjects that are not responders to the therapy of interest. Then, a new plurality of subjects is identified for the clinical trial for the therapy of interest based on matches between cellular constituent values for the revised set of discriminating cellular constituents in the first set of subjects in the plurality of subjects that are responders to the therapy of interest and the molecular profiles of the first plurality of subjects.

In some aspects of the invention, the method further comprises observing a progression of a disease in each subject in the first plurality of subjects and storing the progression of the disease in each subject in the first plurality of subjects (e.g., in a database). In some such embodiments, the method further comprises (i) removing the molecular profile of a subject from the candidate set when the progression of the disease in the subject does not satisfy a selection criterion (e.g., failure to respond to a therapy other than the therapy of interest, responsiveness to a therapy other than the therapy of interest, failure to respond to the therapy of interest, responsiveness to the therapy of interest, etc.) and retaining the molecular profile of a subject in the candidate set when the progression of the disease in the subject satisfies the selection criterion. In some embodiments, the observation of the progression of the disease comprises completing a web-based questionnaire.

In some aspects of the invention, the method further comprises administering to a subject in the plurality of subjects the therapy of interest and storing: a record of the therapy of interest in a record associated with the subject. In some embodiments, this storing step comprises completing a web-based questionnaire. In some embodiments, the method further comprises obtaining a biological sample in the plurality of biological samples from a remote location. In some embodiments, the obtaining step comprises entering patient data or clinical data associated with the biological sample into a web-based questionnaire at the remote location.

Still another aspect of the invention comprises a computer program product for use in conjunction with a computer system. Here, the computer program product comprises a computer readable storage medium and a computer program mechanism embedded therein. The computer program mechanism identifies a plurality of subjects for a clinical trial for a therapy of interest through computer encoded instructions that include instructions for identifying a candidate set of molecular profiles in a stored first plurality of molecular profiles, where each molecular profile in the candidate set of molecular profiles has measurements for a discriminating set of cellular constituents that match the measurements of the discriminating set of cellular constituents in a responder set of biological samples. In this way, the plurality of subjects for the clinical trial from those subjects from which the candidate set of molecular profiles were derived is identified. In this aspect of the invention, each respective molecular profile in the stored first plurality of molecular profiles comprises measurements of a first plurality of cellular constituents from a respective biological sample in a first plurality of biological samples obtained from a first plurality of subjects and the discriminating set of cellular constituents is identified from those cellular constituents in the first plurality of cellular constituents whose measurement values taken prior to exposure to the therapy of interest discriminates between the responder set of biological samples and a nonresponder set of biological samples.

Another aspect of the present invention comprises a computer having a central processing unit and a memory coupled to the central processing unit, the memory storing a module for identifying a plurality of subjects for a clinical trial for a therapy of interest. The module comprises instructions for identifying a candidate set of molecular profiles in a stored first plurality of molecular profiles, where each molecular profile in the candidate set of molecular profiles has measurements for a discriminating set of cellular constituents that match the measurements of the discriminating set of cellular constituents in a responder set of biological samples, thereby identifying the plurality of subjects for the clinical trial from those subjects from which the candidate set of molecular profiles were derived. Each respective molecular profile in the stored first plurality of molecular profiles comprises measurements of a first plurality of cellular constituents from a respective biological sample in a first plurality of biological samples obtained from a first plurality of subjects. The discriminating set of cellular constituents is identified from those cellular constituents in the first plurality of cellular constituents whose measurement values taken prior to exposure to the therapy of interest discriminates between the responder set of biological samples and a nonresponder set of biological samples.

Still another aspect of the invention provides a method of identifying a plurality of subjects for a clinical trial for a therapy of interest. The method comprises measuring a molecular profile for each biological sample in a first plurality of biological samples thereby obtaining a first plurality of molecular profiles, where the first plurality of biological samples are obtained from a first plurality of subjects and each respective molecular profile in the first plurality of molecular profiles comprises measurements of a first plurality of cellular constituents from a respective biological sample in the first plurality of biological samples. The first plurality of molecular profiles are stored. A molecular profile for each biological sample in a second plurality of biological samples is measured prior to exposure to the therapy of interest, thereby obtaining a second plurality of molecular profiles, where each biological sample in the second plurality of biological samples is from a subject having a disease of interest or is a model for the disease of interest and each respective molecular profile in the second plurality of molecular profiles comprises measurements of two or more of the first plurality of cellular constituents from a respective biological sample in the second plurality of biological samples. A responder set of biological samples is determined that are responders to the therapy of interest for the disease of interest in the second plurality of biological samples and a nonresponder set of biological samples is determined that are nonresponders to the therapy of interest for the disease of interest in the second plurality of biological samples. A discriminating set of cellular constituents in the first plurality of cellular constituents is then identified, where the measurements in the second plurality of molecular profiles for each respective cellular constituent in the discriminating set of cellular constituents discriminates between the responder set of biological samples and the nonresponder set of biological samples. A candidate set of molecular profiles is identified in the stored first plurality of molecular profiles that have measurements for the discriminating set of cellular constituents that match the measurements of the discriminating set of cellular constituents in the responder set of biological samples, thereby identifying the plurality of subjects for the clinical trial from those subjects from which the candidate set of molecular profiles were derived.

In some embodiments, the first plurality of cellular constituents comprises more than five thousand cellular constituents. In some embodiments, the molecular profile for each biological sample in the first plurality of biological samples is obtained using a microarray that comprises oligonucleotides representing more than thousand cellular constituents, more than two thousand cellular constituents, more than three thousand cellular constituents, more than four thousand cellular constituents, more than five thousand cellular constituents, between three thousand and ten thousand cellular constituents, or less than twenty-five thousand cellular constituents. In some embodiments, a cellular constituent in the discriminating set of cellular constituents is a nucleic acid or a protein. In some embodiments, each biological sample in the second plurality of biological samples is a cell line and/or is obtained from a subject in a second plurality of subjects. In some embodiments, each biological sample in the second plurality of biological samples is a portion of a tumor. In some embodiments, the second plurality of molecular profiles consists of less than one hundred molecular profiles and the first plurality of molecular profiles comprises more than five hundred molecular profiles. In some embodiments, measurements for a cellular constituent in the set of discriminating set of cellular constituents discriminates with a p value of less than 0.05 as determined by a parametric or nonparametric test using measurements for the cellular constituent in the molecular profiles of the responder set of biological samples and measurements for the cellular constituent in the molecular profiles of the nonresponder set of biological samples. In some embodiments, the therapy of interest is exposure to a drug, exposure to radiation, exposure to radio-frequency ablation, or exposure to an siRNA. In some embodiment, the first plurality of subjects are human, bovine (cow), porcine, canine, feline (cat), ovine (sheep), equine, lapine (rabbit), hamster, chicken, rat, mouse, chimpanzee, or baboon.

Another aspect of the invention comprises a computer program product for use in conjunction with a computer system, where the computer program product comprises a computer readable storage medium and a computer program mechanism embedded therein. The computer program mechanism is for identifying a plurality of subjects for a clinical trial for a therapy of interest and comprises instructions for receiving a molecular profile for each biological sample in a first plurality of biological samples thereby obtaining a first plurality of molecular profiles. The first plurality of biological samples are obtained from a first plurality of subjects and each respective molecular profile in the first plurality of molecular profiles comprises measurements of a first plurality of cellular constituents from a respective biological sample in the first plurality of biological samples. The first plurality of molecular profiles is stored. The computer program mechanism further comprises instructions for receiving a molecular profile for each biological sample in a second plurality of biological samples prior to exposure to the therapy of interest, thereby obtaining a second plurality of molecular profiles, where each biological sample in the second plurality of biological samples is from a subject having a disease of interest or is a model for the disease of interest and each respective molecular profile in the second plurality of molecular profiles comprises measurements of two or more of the first plurality of cellular constituents from a respective biological sample in the second plurality of biological samples. The computer program mechanism further comprises instructions for determining a responder set of biological samples that are responders to the therapy of interest for the disease of interest in the second plurality of biological samples and a nonresponder set of biological samples that are nonresponders to the therapy of interest for the disease of interest in the second plurality of biological samples. The computer program mechanism further comprises instructions for finding a discriminating set of cellular constituents in the first plurality of cellular constituents, where the measurements in the second plurality of molecular profiles for each respective cellular constituent in the discriminating set of cellular constituents discriminates between the responder set of biological samples and the nonresponder set of biological samples. The computer program mechanism further comprises, instructions for identifying a candidate set of molecular profiles in the stored first plurality of molecular profiles that have measurements for the discriminating set of cellular constituents that match the measurements of the discriminating set of cellular constituents in the responder set of biological samples. Execution of these instructions identifies the plurality of subjects for the clinical trial from those subjects from which the candidate set of molecular profiles were derived.

Still another aspect of the invention provides a computer comprising a central processing unit and a memory coupled to the central processing unit. The memory stores a module for identifying a plurality of subjects for a clinical trial for a therapy of interest. The module comprises instructions for receiving a molecular profile for each biological sample in a first plurality of biological samples thereby obtaining a first plurality of molecular profiles, where the first plurality of biological samples are obtained from a first plurality of subjects and each respective molecular profile in the first plurality of molecular profiles comprises measurements of a first plurality of cellular constituents from a respective biological sample in the first plurality of biological samples as well as instructions for storing the first plurality of molecular profiles. The module further comprises instructions for measuring a molecular profile for each biological sample in a second plurality of biological samples prior to exposure to the therapy of interest, thereby obtaining a second plurality of molecular profiles, where each biological sample in the second plurality of biological samples is from a subject having a disease of interest or is a model for the disease of interest and each respective molecular profile in the second plurality of molecular profiles comprises measurements of two or more of the first plurality of cellular constituents from a respective biological sample in the second plurality of biological samples. The module further comprises instructions for determining a responder set of biological samples that are responders to the therapy of interest for the disease of interest in the second plurality of biological samples and a nonresponder set of biological samples that are nonresponders to the therapy of interest for the disease of interest in the second plurality of biological samples. The module further comprises instructions for finding a discriminating set of cellular constituents in the first plurality of cellular constituents, where the measurements in the second plurality of molecular profiles for each respective cellular constituent in the discriminating set of cellular constituents discriminates between the responder set of biological samples and the nonresponder set of biological samples. The module further comprises instructions for identifying a candidate set of molecular profiles in the stored first plurality of molecular profiles that have measurements for the discriminating set of cellular constituents that match the measurements of the discriminating set of cellular constituents in the responder set of biological samples. Execution of these instructions identifies the plurality of subjects for the clinical trial from those subjects from which the candidate set of molecular profiles were derived.

4. BRIEF DESCRIPTION OF THE DRAWINGS

FIG. 1 illustrates a computer system for selecting subjects for clinical trials in accordance with an embodiment of the present invention.

FIG. 2. illustrates a method for selecting subjects for clinical trials in accordance with an embodiment of the present invention.

FIG. 3. illustrates a data structure for storing a clinical features of a patient in accordance with an embodiment of the present invention.

FIG. 4 illustrates a data structure for storing a demographic characterization of a patient in accordance with an embodiment of the present invention.

FIG. 5 illustrates a questionnaire that can be used to enter patient information in accordance with an embodiment of the present invention following surgery.

FIG. 6 illustrates information that can be provided by a medical oncologist following treatment, in accordance with an embodiment of the present invention.

FIG. 7A illustrates a metastatic follow-up form that is filled out by a medical in accordance with an embodiment of the present invention.

FIG. 7B illustrates a form that is filled out by a medical practitioner following a primary resection in accordance with an embodiment of the present invention.

FIG. 8 illustrates a data structure in which successive molecular profiles can be stored in accordance with an embodiment of the present invention.

Like reference numerals refer to corresponding parts throughout the several views of the drawings.

5. DETAILED DESCRIPTION

Figure 1:
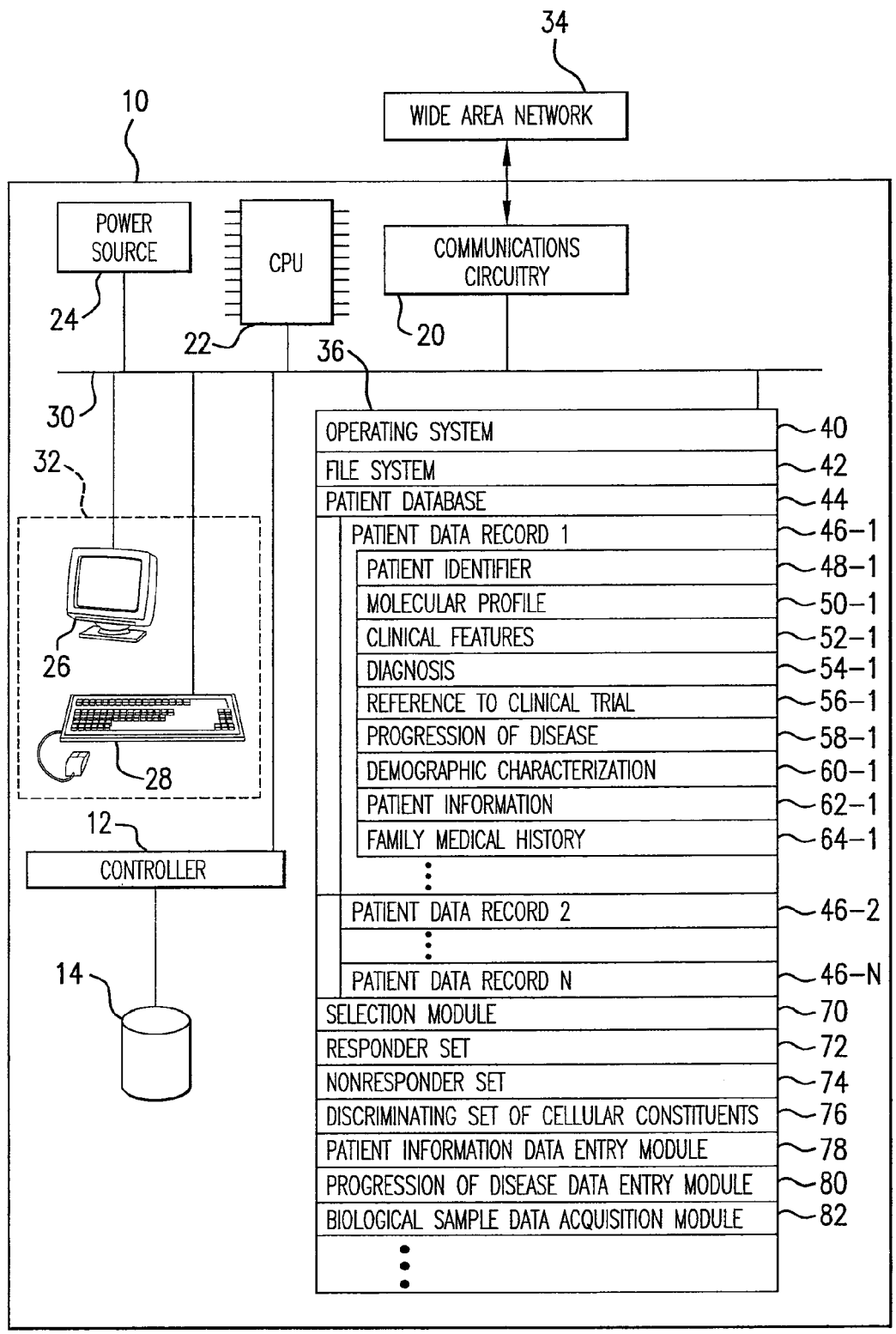

Computers, computer program products, systems, and methods for identifying a plurality of subjects for a clinical trial are provided. A candidate set of molecular profiles in a stored plurality of molecular profiles are identified. Each such profile has measurements for a discriminating set of cellular constituents that match the measurements of corresponding cellular constituents in a responder set of biological samples. In this way, the plurality of subjects for the trial is identified from those subjects from whom the candidate set of molecular profiles were derived. Each respective molecular profile in the stored plurality of profiles has measurements of a plurality of cellular constituents from a respective biological sample in a plurality of samples obtained from a first plurality of subjects. The discriminating set of cellular constituents is identified from those cellular constituents in the plurality of cellular constituents whose measurement values discriminates between the responder and nonresponder sets of biological samples.

One application of such computers, computer program products, systems and methods is the identification of specific diseases/conditions for which a given chemical agent or pharmaceutical drug would provide effective therapeutic treatment. For example, the present invention provides systems and methods for identifying specific cancers for which currently available chemical agents, pharmaceutical drugs, or other therapies of interest would provide effective treatment. In one embodiment, the subject invention provides systems and methods for defining molecular profiles for at least two specific disease states (e.g., cancers) to establish a screenable database of gene expression signatures, (2) identifying a therapy of interest (e.g., one or more chemical agents or one or more pharmaceutical drugs) known to be therapeutically effective in treating a specific disease state whose expression signature is defined by the database, (3) defining a discrimination set of cellular constituents that are representative of changes in expression signatures or "response signature" for the molecular profile of the specific disease state after administration of the therapy of interest induces a therapeutic effect; and (4) analyzing the screenable database to identify any other disease states that include a similar response signature for which the therapy of interest may be therapeutically effective in treating.

In one embodiment, molecular profiles for specific diseases (e.g., cancers) are identified and stored in a screenable database in accordance with the subject invention. A therapy of interest that is known to be therapeutically effective for a specific disease is selected. A biological sample for which the therapy of interest is known to therapeutically affect is then exposed to the therapy of interest and its molecular profile is obtained. This molecular profile may be measurements of cellular constituents in the biological sample prior to exposure. Alternatively, this molecular profile may be differential measurements of cellular constituents in the biological sample before and after exposure to the therapy of interest, where a change in the expression of specific cellular constituents serves as a "response signature" for the change in cellular response to the therapy of interest. The use of response signatures in screening the database expands the number of disease states that can be searched or identified for which the therapy of interest would be therapeutically effective in treating.

FIG. 1 details an exemplary system that supports the functionality described above. The system is preferably a computer system 10 having:

- a central processing unit 22;
- a main non-volatile storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28) and a display 26 as well as other input and output devices (e.g., a mouse);
- a network interface card 20 for connecting to any wired or wireless communication network 34 (e.g., a wide area network such as the Internet);
- an internal bus 30 for interconnecting the aforementioned elements of the system; and
- a power source 24 to power the aforementioned elements.

Operation of computer 10 is controlled primarily by operating system 40, which is executed by central processing unit 22. Operating system 40 can be stored in system memory 36. In a typical implementation, system memory 36 includes:

- file system 42 for controlling access to the various files and data structures used by the present invention;
- a patient database 44 for storing molecular profiles and other information for a first plurality of subjects;
- a selection module for identifying a plurality of subjects for a clinical trial for a therapy of interest;
- information about a responder set 72 of biological samples that are known to respond to a therapy of interest;
- information about a nonresponder set 74 of biological samples that are known to not respond to a therapy of interest;
- information about a discriminating set of cellular constituents 76 whose abundance values in the responder set 72 and in the nonresponder set 74 are such that they can be used to discriminate between presence in the responder set 72 and in the nonresponder set 74;
- a patient information data entry module 78 for collecting information about subjects in patent database 44;
- a progression of disease data entry module 80 for collecting information about progression of disease in subjects in patent database 44; and
- a biological sample data acquisition module 82 for collecting information about biological samples (e.g., tumors) from subjects in patent database 44.

As illustrated in FIG. 1, computer 10 comprises patient database 44. Database 44 can be any form of data storage system including, but not limited to, a flat file, a relational database (SQL), and an on-line analytical processing (OLAP) database (MDX and/or variants thereof). In some specific embodiments, database 44 is a hierarchical OLAP cube. In some specific embodiments, database 44 comprises a star schema that is not stored as a cube but has dimension tables that define hierarchy. Still further, in some embodiments, patient database 44 has hierarchy that is not explicitly broken out in the underlying database or database schema (e.g., dimension tables are not hierarchically arranged). In some embodiments, patient database 44 is a single database that includes patient data. In other embodiments, patient database 44 in fact comprises a plurality of databases that may or may not all be hosted by the same computer 10. In such embodiments, some component databases of patient database 44 are stored on computer systems that are not illustrated by FIG. 1 but that are addressable by wide area network 34. It will be appreciated that many of the modules illustrated in FIG. 1 can be located on one or more remote computers. For example, some embodiments of the present application are web service-type implementations. In such embodiments, patient information data entry module 78, progression of disease data entry module 80, biological sample data acquisition module 82, and other modules used by a physician or clinical worker can reside on a client computer that is in communication with computer 10 via network 34. In some embodiments, for example, patient information data entry module 78, progression of disease data entry module 80, biological sample data acquisition module 82 can each be an interactive web page.

In some embodiments, the database 44 and modules (e.g. modules 70, 78, 80, and 82) illustrated in FIG. 1 are on a single computer (computer 10) and in other embodiments the database 44 and modules are hosted by several computers (not shown). Any arrangement of database 44 and the modules illustrated in FIG. 1 on one or more computers is within the scope of the present invention so long as these components are addressable with respect to each other across network 34 or other electronic means (e.g., wireless means). Thus, the present invention fully encompasses a broad array of computer systems.

The present invention can be implemented as a computer program product that comprises a computer program mechanism embedded in a computer readable storage medium. For instance, the computer program product could contain the program modules shown in FIG. 1. These program modules may be stored on a CD-ROM, DVD, magnetic disk storage product, or any other computer readable data or program storage product. The software modules in the computer program product can also be distributed electronically, via the Internet or otherwise, by transmission of a computer data signal (in which the software modules are embedded) on a carrier wave.

One aspect of the present invention comprises computer systems that can carry out any of the methods, or parts thereof, disclosed in this application. Another aspect of the present invention comprises computer program products that can carry out any of the methods, or parts thereof, disclosed in this application.

5.2. Exemplary Patient Database

Now that an overview of the components of a system in accordance with the present invention has been described, a more detailed description of a patient database 44 in accordance with one aspect of the invention follows. Patient database 44 includes a plurality of patient records 46. There is no limit on the number of patient records 46 that can be held in patient database 44. Database 44 can hold as few as one patient record 46. More typically, database 44 holds between 1 and 100 patient records, more than 100 patient records, more than a thousand patient records, more than ten thousand patient records, more than 100 thousand patient records, or between 1 patient record and one million patient records. Each patient record 46 preferably, but only optionally, includes a patient identifier 48. As those skilled in the database arts will appreciate, a patient identifier 48 need not be explicitly enumerated in certain database systems. For instance, in some systems, a patient identifier 48 can simply be a patient record 46 identifier. However, in some embodiments, a patient identifier 48 can be a number that uniquely identifies a patient within a health care program.

An advantage of database 44 is that it has the capability of tracking molecular profile information 50 and clinical features 52 for each patient registered in database 44. In some embodiments, a molecular profile 50 is the abundance levels of a plurality of cellular constituents in a biological sample obtained from the patient. In some embodiments, such abundance levels are normalized using any of the techniques disclosed in Section 5.6. In some embodiments, a molecular profile is obtained using a microarray. In some embodiments, and of the techniques disclosed in Sections 5.8 or 5.9 may be used to obtain a molecular profile.

Representative biological samples include, but are not limited to, blood, a component of blood, a portion of a tumor, plasma, serum, saliva, sputum, urine, cerebral spinal fluid, cells, a cellular extract, a tissue specimen, a tissue biopsy, or a stool specimen. In some embodiments a biological sample is whole blood and this whole blood is used to obtain measurements for a biomarker profile. In some embodiments a biological sample is some component of whole blood. For example, in some embodiments some portion of the mixture of proteins, nucleic acid, and/or other molecules (e.g., metabolites) within a cellular fraction or within a liquid (e.g., plasma or serum fraction) of the blood. In some embodiments, the biological sample is whole blood but the biomarker profile is resolved from biomarkers expressed or otherwise found in monocytes that are isolated from the whole blood. In some embodiments, the biological sample is whole blood but the biomarker profile is resolved from biomarkers expressed or otherwise found in red blood cells that are isolated from the whole blood. In some embodiments, the biological sample is whole blood but the biomarker profile is resolved from biomarkers expressed or otherwise found in platelets that are isolated from the whole blood. In some embodiments, the biological sample is whole blood but the biomarker profile is resolved from biomarkers expressed or otherwise found in neutrophils that are isolated from the whole blood. In some embodiments, the biological sample is whole blood but the biomarker profile is resolved from biomarkers expressed or otherwise found in eosinophils that are isolated from the whole blood. In some embodiments, the biological sample is whole blood but the biomarker profile is resolved from biomarkers expressed or otherwise found in basophils that are isolated from the whole blood. In some embodiments, the biological sample is whole blood but the biomarker profile is resolved from biomarkers expressed or otherwise found in lymphocytes that are isolated from the whole blood. In some embodiments, the biological sample is whole blood but the biomarker profile is resolved from biomarkers expressed or otherwise found in monocytes that are isolated from the whole blood. In some embodiments, the biological sample is whole blood but the biomarker profile is resolved from one, two, three, four, five, six, or seven cell types from the group of cells types consisting of red blood cells, platelets, neutrophils, eosinophils, basophils, lymphocytes, and monocytes. In some embodiments, a biological sample is a tumor that is surgically removed from the patient, grossly dissected, and snap frozen in liquid nitrogen within twenty minutes of surgical resection.

In some embodiments, a molecular profile 50 comprises the processed microarray image data from the biological specimen obtained from the patient. In one example, molecular profile data 50 comprise cellular constituent abundance information for all or a portion of the cellular constituents represented in a microarray, optional background signal information, and optional associated annotation information describing the probe used for the respective cellular constituent. As used herein, the term "cellular constituent" comprises individual genes, proteins, mRNA, RNA, and/or any other variable cellular component or protein activity, degree of protein modification (e.g., phosphorylation), for example, that is typically measured in a biological experiment by those skilled in the art.

In some embodiments, a molecular profile 50 represents the transcriptional state of cellular constituents in a biological specimen. See, for example, Section 5.8 below. However, in other embodiments, a molecular profile can track aspects of the biological state other than or in addition to transcriptional state. Such other aspects of the biological state include, but are not limited to, the translational state, the activity state of cellular constituents in a biological sample. See, for example, Section 5.9, below. In some embodiments, for example, molecular profile data 50 is, in fact, protein levels for various proteins in the biological specimen from the patient. Thus, in some embodiments, molecular profiles 50 comprise amounts or concentrations of the cellular constituent in biological specimens, cellular constituent activity levels in biological specimens, the state of cellular constituent modification (e.g., phosphorylation) in biological specimens, or other measurements.

In one embodiment, the amount of at least one cellular constituent that is tracked in a molecular profile 50 comprises abundances of at least one RNA species present in one or more cells in the biological specimen obtained from the patient. Such abundances can be measured by a method comprising contacting a gene transcript array with RNA derived from one or more cells of the biological specimen, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species. In one particular embodiment, the abundance of the RNA is measured by contacting a gene transcript array with the RNA from one or more cells of the biological specimen, or with nucleic acid derived from the RNA, such that the gene transcript array comprises a positionally addressable surface with attached nucleic acids or nucleic acid mimics, where the nucleic acids or nucleic acid mimics are capable of hybridizing with the RNA species, or with nucleic acid derived from the RNA species.

In some embodiments, a molecular profile 50 can include abundance information or activity information about ten or more, 500 or more, 1000 or more, or 5000 or more cellular constituents (e.g., genes or proteins), between ten and one thousand cellular constituents, between one thousand and twenty thousand cellular constituents, or more than twenty thousand cellular constituents. In some embodiments, in addition to or rather than providing abundance information or activity information for cellular constituents, a molecular profile 50 tracks cellular constituent marker information. Such genetic marker information includes, but is not limited to, single nucleotide polymorphisms (SNPs), SNP haplotypes, microsatellite markers, restriction fragment length polymorphisms (RFLPs), short tandem repeats, sequence length polymorphisms, DNA methylation, random amplified polymorphic DNA (RAPD), amplified fragment length polymorphisms (AFLP), and "simple sequence repeats." For more information on molecular marker methods, see generally, *The DNA Revolution* by Andrew H. Paterson 1996 (Chapter 2) in: *Genome Mapping in Plants* (ed. Andrew H. Paterson) by Academic Press/R. G. Landis Company, Austin, Tex., 7-21.

SNPs occur approximately once every 600 base pairs in the genome. See, for example, Kruglyak and Nickerson, 2001, *Nature Genetics* 27:235. Alleles making up blocks of such SNPs in close physical proximity are often correlated, resulting in reduced genetic variability and defining a limited number of "SNP haplotypes" each of which reflects descent from a single ancient ancestral chromosome. See Fullerton et al., 2000, *Am. J. Hum. Genet.* 67:881. Such haplotype structure is used in some embodiments of the present invention. Patil et al. found that a very dense set of SNPs is required to capture all the common haplotype information. See Patil et al., 2001, *Science* 294:1719-1723. DNA methylation is described in Grunau et al., 2003, *Nucleic Acids Res.* 31:75-77.

RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. As a result, restriction fragments from homologous chromosomes are revealed. Differences in fragment size among alleles represent an RFLP (see, for example, Helentjaris et al., 1985, *Plant Mol. Bio.* 5:109-118, and U.S. Pat. No. 5,324,631).

The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland, 1990, *Nucleic Acids Res.* 18:7213-7218; Hu and Quiros, 1991, *Plant Cell Rep.* 10:505-511). AFLP technology refers to a process that is designed to generate large numbers of randomly distributed molecular markers (see, for example, European Patent Application No. 0534858 A1).

"Simple sequence repeats" or "SSRs" are di-, tri- or tetra-nucleotide tandem repeats within a genome. The repeat region can vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al., 1996, *Theor. Appl. Genet.* 93:1071-1077; Bligh et al, 1995, *Euphytica* 86:83-85; Struss et al., 1998, *Theor. Appl. Genet.* 97:308-315; Wu et al., 1993, *Mol. Gen. Genet.* 241:225-235; and U.S. Pat. No. 5,075,217). SSR are also known as satellites or microsatellites.

In some embodiments of the present invention, in addition to molecular profiles 50, patient records 46 optionally includes clinical features 52 for patients 46. In some embodiments, a clinical feature is the absence or presence of a disease in a patient 46. In some embodiments, the disease is arthritis, asthma, an allergy, cancer, chronic fatigue syndrome, diabetes, epilepsy, heart disease, hemochromatosis, hepatitis B, hepatitis C, or osteoporosis. In some embodiments, the disease is breast cancer, cervical cancer, colorectal cancer, lung cancer, oral cancer, ovarian cancer, prostate cancer, skin cancer, or testicular cancer. In some embodiments, the disease is any of the diseases set forth in Section 5.10. In some embodiments, the clinical feature is ankle swelling, anorexia, dyspnoea, fatigue, high blood pressure, hypoxemia, lethargy, lymphopenia, nocturnal cough, nocturnal dyspnoea, obesity, orthopnoea, paroxysmal, a viral infection, reduced exercise tolerance, tachycardia, tachypnea, or wheeze. In some embodiments, the clinical feature 52 comprises observations made by a patient's physician. In some instances, the observations made by a physician include a code from the International Classification of Diseases, $9^{th}$ Revision, prepared by the Department of Health and Human Services (ICD-9 codes), or an equivalent, and dates such observations were made.

FIG. 3 illustrates a clinical features data structure 52 in accordance with one embodiment of the present invention. The data structure includes an ICD-9 code (302) for each patient ailment and each corresponding date 304 such characterizations were made. Clinical features 52 complements information found within molecular profile 50. The clinical feature 52 can include laboratory test results (e.g., cholesterol level, high density lipoprotein/low density lipoprotein ratios, triglyceride levels, etc.), statements made by the patient about their health, x-rays, biopsy results, and any other medical information typically relied upon by a doctor to make a diagnosis of the patient.

Patients enrolled in health care programs in accordance with the present invention preferably have the opportunity to enroll in clinical trials that are designed to test, discover and/or optimize application of one or more drugs or other forms of treatment regimens. As such, patient record 46 can optionally include a reference 56 to a clinical trial to which the patient is enrolled. Furthermore, patient record 46 can store, reference, or otherwise include the results and/or clinical outcome of such a clinical trial. In some embodiments, information regarding the clinical trial itself is stored in commercial clinical trial products sold by companies such as InferMed, Ltd., London UK, Phase Forward Inc., Waltham, Mass., CB Technology, Philadelphia, Pa., DataTRAK Cleveland, Ohio, Araccel, Stockholm, Sweden, and TEAMworks, Hannover, Germany.

Patient records 46 can optionally further include patient information 62. Such patient information 62 may include a diagnosis 54, a progression of disease 58, demographic characterization 60, family medical history 64, or subject treatment history. A diagnosis 54 represents the diagnosis for the patient corresponding to the patient data record 46 given by a doctor. Progression of disease 58 comprises observations made by medical or clinical professionals on the progression of a disease in a subject over time. Demographic characterization 60 includes demographic information about subjects 46. Referring to FIG. 4, in some embodiments, the demographic characterization for a respective patient comprises, for example, any combination of a gender 402 of the patient, a marital status 404 of the patient, an ethnicity 406 of the patient, a primary language 408 spoken by the patient, the color of the eyes 410 of the patient, the hair color 412 of the patient, the height 414 of the patient, the weight 416 of the patient, the social security number 418 of the patient, the name 420 of the patient, the date of birth 422 of the patient, the educational status 424 of the patient, an identity of the primary physician 426 for the patient, a name of a referring physician 428 for the patient, a referral source 430 for the patient, an indication 432 as to whether the patient is disabled and a description of the disability, an indication 434 as to whether the patient is a smoker, an indication 436 as to whether the patient consumes alcohol, a residential address 438 of the patient, and/or a telephone number 440 of the patient. In addition, the demographic characterization 60 can include a name of an insurance carrier 442 for an insurance policy held by the patient and/or a member identifier number 444 for an insurance policy held by the patient.

In some embodiments, patient (subject) information includes, for example, any combination of an address where the subject lives, next of kin contact information, a telephone number for the subject, an age of the subject, an allergy of the subject, a height of the subject, a weight of the subject, a race of the subject, insurance information for the subject, subject treatment history, a diagnosis of the subject, or family medical history for the subject.

In some embodiments, a patient data record 46 includes a family medical history 64 in order to guide the selection of an appropriate treatment regimen for the patient. Family medical history 64 can include data such as whether or not a member of the patient's family has a disease, the molecular profile of biological samples taken from family members and the like.

In some embodiments, a patient data record 46 includes subject treatment history. Subject treatment history 62 indicates the treatment given to a patient and when such treatment was given. Subject treatment history 62 includes all prescriptions given to the patient and all medical procedures undergone on the patient. In some embodiments, the medical procedures include Current Procedural Terminology (CPT) codes developed by the American Medical Association for the procedures performed on the patient and a date such procedures were performed on the patient. Subject treatment history may include pathology data (e.g., world health organization (classification, tumor, nodes, metastases staging, images), radiographic images (e.g., raw, processed, cat scans, positron emission tomography), demographic data 60 (e.g., age, sex, etc.), laboratory data, Cerner electronic medical record data (hospital based data), risk factor data, access to a clinical reporting and data system, reference to vaccine production data/quality assurance, reference to a clinical data manager (e.g., OPTX), and/or reference to a cancer registry such as a research specimen banking database.

Advantageously, in some embodiments, patient information is entered electronically through a web-based questionnaire and/or a Galvanon (Maitland, Fla.) hospital kiosk solution. FIG. 9 illustrates representative screenshots of portions of such questionnaires.

5.3. Exemplary Methods

Now that an overview of a system in accordance with one embodiment of the present invention has been described, various advantageous methods that can be used in accordance with the present invention will now be disclosed in this section. The goal of such methods is to identify a plurality of subjects for a clinical trial for a therapy of interest (e.g., exposure to a drug, exposure to radiation, exposure to radiofrequency ablation, or exposure to an siRNA, etc.). In some embodiments, the plurality of subjects are human, bovine, porcine, canine, feline, ovine, equine, lapine, hamster, chicken, rat, mouse, chimpanzee, or baboon. In some embodiments, the clinical trial is a prevention trial, screening trial, quality-of-life trial, a treatment trial (phase I, II, or III), or a diagnostic trial.

Prevention clinical trials look for ways to reduce the risk of developing a particular disease or preventing it from coming back. These trials test the usefulness of certain medicines, vitamins, minerals or other supplements. The medicine or supplement that is chosen for a clinical trial is one that researchers believe may be able to lower cancer risk. Other prevention trials explore whether exercise, quitting smoking, eating more vegetables and fruit or other lifestyle choices help to prevent the disease.

Screening clinical trials test or evaluate the best ways to detect the disease, especially in its early stages. In some cases, detecting the disease early can improve the results of treatment and increase the chances of survival. One example of a screening trial is the study of new medical imaging methods. Another example might be a new type of blood test that would detect clues that, for example, cancer can be present in a person's body. These trials usually involve subjects who may be at higher-than-average risk of developing the disease.

Quality-of-life clinical trials (also called supportive care trials) study how to improve comfort levels and quality of life for subjects with a disease and disease survivors. For example, these trials may look at better ways to prevent or manage nausea, fatigue, depression, pain or other problems caused by the disease or its treatment.

Treatment clinical trials involve subjects with the disease. These trials usually compare new disease treatments with ones that already exist. The trials can be designed to answer issues such as (i) does the new treatment work better than the current best standard of care, (ii) will the new treatment reduce the chance that the disease will spread or come back, (iii) does the new treatment have fewer side effects than the current standard of treatment, and (iv) do most patients tolerate the side effects from the new treatment better. Therapies tested in treatment clinical trials for cancer include, but are not limited to, (i) surgery—testing new techniques and timing of surgical procedures, (ii) chemotherapy—testing new drugs, drug combinations, different dosages and schedules of taking the drugs, (iii) hormone therapy—testing new ways to protect subjects with disease from the effects of various hormones on the disease, (iv) radiation therapy—testing new methods of delivering radiation or combining radiation with other disease therapies, (v) immunotherapy and vaccines— testing new treatments to stimulate and restore the body's own defenses, and developing vaccines against a particular type of disease, (vi) bone marrow and stem cell transplants— testing ways to protect the body while delivering more effective doses of chemotherapy or radiation, and (vii) anti-angiogenesis—studies drugs that kill cancers by blocking the growth of blood vessels that supply tumors.

Treatment clinical trials are carried out in steps called "phases", the most prominent of which are phases I, II, and III. Phase I treatment trials are primarily concerned with assessing the safety of a drug. Phase I testing in humans is typically done in about 20 to 100 healthy volunteers. A phase I clinical study is designed to determine what happens to the drug in the patient. That is, how it is absorbed, metabolized, and excreted. In addition, by measuring the side effects of the drug at various dosage levels, a phase I study provides information on optimal drug dosage.

While a phase I treatment trial is directed to drug safety, a phase II treatment trial is directed to drug efficacy. A phase II treatment trial occurs after successful completion of a phase I treatment trial. A phase II treatment trial can last from several months to two years, and involve up to several hundred patients at numerous clinical sites throughout the world. Most phase II treatment trials are randomized trials. One group of patients receives the experimental drug while a control group receives a placebo or best standard treatment available. Often phase II treatment trials are "blinded" in the sense that neither the patients nor the researchers know who is getting the experimental drug. In this manner, the phase II treatment trial can provide a pharmaceutical company and a regulatory body, such as the United States Food and Drug Administration (FDA) of the United States or the European Commission (EC) of the European Union, comparative information about the efficacy of the new drug. If the phase II treatment trial is successful, a phase III treatment trial can be authorized. In some instances, marketing approval can be obtained based on a phase II trial, with a phase III trial following post-approval.

Typically, in a phase III treatment trial, the new drug is tested in several hundred to several thousand patients at hundreds of clinical sites throughout the world. This large-scale testing provides hospitals, pharmaceutical companies, and the regulatory agency with a more thorough understanding of the drug's effectiveness, benefits, and the range of possible adverse reactions. Most phase III treatment trials are randomized and blinded trials. Phase III treatment trials typically last several years.

One aspect of the present invention provides systems, methods, and apparatus for identifying a plurality of subjects for a clinical trial for a therapy of interest. A candidate set of molecular profiles in a stored first plurality of molecular profiles is identified. The candidate set of molecular profiles can include, for example, between two and 100 molecular profiles, more than five molecular profiles, more than twenty molecular profiles, more than one hundred molecular profiles, more than one thousand molecular profiles, or more than five thousand molecular profiles. Each molecular profile in the candidate set of molecular profiles has measurements for a discriminating set of cellular constituents that match the measurements of the discriminating set of cellular constituents in a responder set of biological samples. In this way, the plurality of subjects for the clinical trial is identified from those subjects from which the candidate set of molecular profiles were derived. Each respective molecular profile in the stored first plurality of molecular profiles comprises measurements of a first plurality of cellular constituents from a respective biological sample in a first plurality of biological samples obtained from a first plurality of subjects.

The first plurality of molecular profiles can include, for example, between two and one hundred molecular profiles, more than five molecular profiles, more than twenty molecular profiles, more than one hundred molecular profiles, more than one thousand molecular profiles, more than ten thousand molecular profiles, more than one hundred thousand molecular profiles, or more than one million molecular profiles. Correspondingly, the first plurality of biological samples can include, for example, between two and one hundred biological sample, more than five biological samples, more than twenty biological samples, more than one hundred biological samples, more than one thousand biological samples, more than ten thousand biological samples, more than one hundred thousand biological samples, or more than one million biological samples. In some embodiments, each molecular profile in the first plurality of molecular profiles is from a different subject. However, in other embodiments, this is not the case. For example, particular molecular profiles in the first plurality of molecular profiles may originate from different tissues of the same subject (e.g., one molecular profile in the first plurality of molecular profiles may originate from the blood of a given subject whereas another molecular profile in the first plurality of molecular profiles may originate from the liver of the same subject).

The first plurality of cellular constituents can include, for example, between ten and one hundred cellular constituents, more than five hundred cellular constituents, more than five thousand cellular constituents, more than ten thousand cellular constituents, more than fifteen thousand cellular constituents, more than twenty thousand cellular constituents, more than twenty-five thousand cellular constituents, or more than thirty thousand cellular constituents. The plurality of subjects identified for the clinical trial can comprise, for example, between ten and one hundred subject, more than forty subjects, more than sixty subjects, more than one hundred subjects, more than two hundred subjects, more than three hundred subjects, more than four hundred subjects, more than five hundred subjects or less than five hundred subjects.

In some embodiments, the discriminating set of cellular constituents is identified from those cellular constituents in the first plurality of cellular constituents whose measurement values taken prior to exposure to the therapy of interest discriminates between the responder set of biological samples and a nonresponder set of biological samples.

A detailed method of the present invention will now be described in conjunction with FIG. 2.

Step 202. In step 202, a molecular profile for each biological sample in a first plurality of biological samples is measured. In this way a first plurality of molecular profiles is obtained. In some embodiments, the first plurality of biological samples comprises two or more biological samples, ten or more biological samples, 100 or more biological samples, 1000 or more biological samples, 10,000 or more biological samples, between 10 and 30,000 biological samples, or less than 30,000 biological samples. Correspondingly, in some embodiments, the first plurality of molecular profiles comprises two or more molecular profiles, ten or more molecular profiles, 100 or more molecular profiles, 1000 or more molecular profiles, 10,000 or more molecular profiles, between 10 and 30,000 molecular profiles, or less than 30,000 molecular profiles. In some embodiments, each molecular profile in the first plurality of molecular profiles is from a different subject. However, in other embodiments, this is not the case. For example, particular molecular profiles in the first plurality of molecular profiles may originate from different tissues of the same subject (e.g., one molecular profile in the first plurality of molecular profiles may originate from the blood of a given subject whereas another molecular profile in the first plurality of molecular profiles may originate from the liver of the same subject).

The first plurality of biological samples is obtained from a first plurality of subjects. Each respective molecular profile in the first plurality of molecular profiles comprises measurements of a first plurality of cellular constituents from a respective biological sample in the first plurality of biological samples. In some embodiments, the first plurality of cellular constituents comprises two or more cellular constituents, ten or more cellular constituents, 100 or more cellular constituents, 1000 or more cellular constituents, 10,000 or more cellular constituents, between 10 and 30,000 cellular constituents, or less than 30,000 cellular constituents. In some embodiments, the first plurality of subjects comprises two or more subject, ten or more subject, 100 or more subjects, 1000 or more subjects, 10,000 or more subjects, between 10 and 30,000 subjects, or less than 30,000 subjects. As used herein, the term "cellular constituent" refers to individual genes, proteins, mRNA, RNA, and/or any other variable cellular component and measurements of cellular constituents can be of abundance, protein activity, degree of protein modification (e.g., phosphorylation), the presence or absence of genetic markers, for example, that can be measured in a biological experiment by those skilled in the art.

In some embodiments, biological samples are obtained from a remote location. In some embodiments, a remote location is a room other than the room where measurements of cellular constituents of the biological samples are made and/or where a candidate set of molecular profiles is stored. In some embodiments, a remote location is a building other than the building where measurements of the cellular constituents of the biological samples are made and/or where a candidate set of molecular profiles is stored. In some embodiments, the remote location is a town, city, state, or country other than the respective town, city, state, or country where the biological measurements are made and/or where a candidate set of molecular profiles is stored. In some embodiments, the remote location is a location that is at least one mile, ten miles, or one hundred miles away from the location where measurements of the cellular constituents of biological samples are made and/or where a candidate set of molecular profiles is stored. In some embodiments, a remote location is a room other than the room that houses computer 10. In some embodiments, a remote location is a building other than the building that houses computer 10. In some embodiments, the remote location is a town, city, state, or country other than the respective town, city, state, or country that houses computer 10. In some embodiments, the remote location is a location that is at least one mile, ten miles, or one hundred miles away from the location that houses computer 10. In some embodiments, the obtaining step further comprises entering patient data or clinical data associated with the biological sample, at the remote location, into a web-based questionnaire or other form of electronic data entry device such as a kiosk.

In some embodiments, the molecular profile for each biological sample in the first plurality of biological samples is obtained using a microarray that comprises oligonucleotides representing more than one hundred cellular constituents, more than five hundred cellular constituents, or more than five thousand cellular constituents.

In some embodiments, the measurements of a first plurality of cellular constituents comprise measurements of protein abundance or nucleic acid abundance. In some embodiments, the measurements of a first plurality of cellular constituents comprise the determination of the absence or presence of one or more genetic markers. Such genetic markers include, but are not limited to, single nucleotide polymorphisms (SNPs), SNP haplotypes, microsatellite markers, restriction fragment length polymorphisms (RFLPs), short tandem repeats, sequence length polymorphisms, DNA methylation, random amplified polymorphic DNA (RAPD), amplified fragment length polymorphisms (AFLP), and "simple sequence repeats." For more information on molecular marker methods, see generally, *The DNA Revolution* by Andrew H. Paterson 1996 (Chapter 2) in: *Genome Mapping in Plants* (ed. Andrew H. Paterson) by Academic Press/R. G. Landis Company, Austin, Tex., 7-21, which is hereby incorporated by reference herein in its entirety.

Step 204. In step 204, the first plurality of molecular profiles is stored. For example, referring to FIG. 1, in some embodiments each molecular profile is stored as a molecular profile 50 in patient database 44. In typical embodiments, steps 202 and 204 occur as part of a long term data retention program rather than for the purpose of enrolling subjects in a specific clinical trial. For this reason, additional information about the subjects that originated the biological samples form which the molecular profiles were measured is often stored along with each molecular profile. Such additional information has been described above in conjunction with FIG. 1. In some embodiments, the information stored in step 204 is part of a multi-site, long term health care initiative such as the Moffitt Total Cancer Care initiative. Thus, in general, storage of molecular profiles and observations means storing the measurements of the cellular constituents represented by such molecular profiles and observations. Such measurements can, for example, be cellular constituent abundance values, an indication of the presence or absence of one or more genetic markers, or any other form of measurement. In some embodiments, such measurements are electronically stored in a computer 10, for example in patient database 44 as electronic records. However, methods are not so limiting. In some embodiments, storage of molecular profiles can be recorded by other means, such as on paper.

Step 206. In step 206, a molecular profile is measured for each biological sample in a second plurality of biological samples prior to exposure to the therapy of interest, thereby obtaining a second plurality of molecular profiles. In some embodiments, each biological sample in the second plurality of biological samples is from a subject having a disease of interest or is a model for the disease of interest. In some embodiments, each biological sample in the second plurality of biological samples is from a subject having the same disease of interest or is a model for the same disease of interest. In some embodiments, biological samples in the second plurality of biological samples may be from subjects having different diseases or serve as models for different diseases. In some embodiments, the subjects from which the second plurality of biological samples is obtained are from more than one species. In some embodiments, the subjects from which the second plurality of biological samples is obtained are all of the same species. In some embodiments, the subjects from which the second plurality of biological samples is obtained (the "second plurality of subjects") are mammals, humans, or non-human mammals. In some embodiments, the second plurality of subjects are human, bovine (cow), porcine, canine, feline (cat), ovine (sheep), equine, lapine (rabbit), hamster, chicken, rat, mouse, chimpanzee, or baboon. In some embodiments, the first plurality of subjects of step 202 is of the same species as the instant second plurality of subjects. In some embodiments the second plurality of subjects is a subset of the first plurality of subjects. In some embodiments, the first plurality of subjects of step 202 is of a different species than the instant second plurality of subjects. In some embodiments, the second plurality of subjects is, in fact, a plurality of biological samples (e.g., portions of tumors, blood samples, and cell lines, etc.).

Each respective molecular profile in the second plurality of molecular profiles comprises measurements of two or more of the first plurality of cellular constituents from a respective biological sample in the second plurality of biological samples. In some embodiments, it is possible that each biological sample in the second plurality of biological samples in fact was from subjects in the first plurality of subjects. In such embodiments, the second plurality of biological samples is identified by screening subjects in patient database 44 in order to identify subjects based one or more predetermined selection criteria. Such predetermined selection criteria may include, for example, presence or absence of a target disease for the therapy of interest, age, health, or sex. In some embodiments, the second plurality of biological samples in fact does not originate from subjects in the first plurality of subjects. In such embodiments, the second plurality of biological samples may be obtained from subjects that likewise satisfy one or more predetermined selection criteria, such as those previously identified.

In some embodiments, the measurements of the two or more of the first plurality of cellular constituents in the molecular profiles in the second plurality of molecular profiles comprises measurements of protein abundance or nucleic acid abundance. In some embodiments, the measurements of the two or more of the first plurality of cellular constituents in the molecular profiles in the second plurality of molecular profiles comprise the determination of the absence or presence of one or more genetic markers.

In some embodiments, each biological sample in said second plurality of biological samples is a cell line. In some embodiments, each biological sample in the second plurality of biological samples is a portion of a tumor. In some embodiments, the second plurality of molecular profiles consists of less than one hundred molecular profiles and the first plurality of molecular profiles comprises more than five hundred molecular profiles.

One aspect of the present invention provides any of the methods disclosed herein wherein the second plurality of molecular profiles consists of less than one hundred molecular profiles and the first plurality of molecular profiles comprises more than five hundred molecular profiles. Another aspect of the present invention provides any of the methods disclosed herein wherein the second plurality of molecular profiles consists of less than 20, 30, 40, 50, 60, 70, 80, 90, 100, 110, 120, 130, 140, 150, 160, 170, 180, 190, or 200 molecular profiles and the first plurality of molecular profiles comprises more than 50, 100, 150, 200, 250, 1000, 5000, or 10000 molecular profiles.

Step 208. In step 208, the therapy of interest is administered to the second plurality of biological samples. Then a responder set of biological samples that are responders to the therapy of interest for the disease of interest is identified in the second plurality of biological samples. Further, a nonresponder set of biological samples that are nonresponders to the therapy of interest for the disease of interest is identified in the second plurality of biological samples. In embodiments where the second plurality of biological samples originate from a second plurality of subjects, the responder set of biological samples comprises those biological samples in the second plurality of biological samples that originate from subjects responsive to the therapy of interest and the nonresponder set of biological samples comprises those biological samples in the second plurality of biological samples that originate from subjects not responsive to the therapy of interest.

In some embodiments, the therapy is a drug and each of the biological samples in the second plurality of biological samples is a cancer cell line. In such embodiments, responsiveness to the therapy is cell death and non-responsiveness is cell survival. In some embodiments, a biological sample is a cancer cell line and it is identified as a responder or nonresponder to a therapy of interest that is a chemotherapeutic by culturing the cell line in the presence of the chemotherapeutic and then assaying for cell survival/death. In such instances death is equated with responsiveness and cell survival is equated with nonresponsiveness. In such embodiments, the focus is then turned to identifying those cellular constituents that discriminate between the cell lines that are responsive and the cell lines that are not responsive. In some embodiments, such discrimination can be, for example, exhibited by differential abundance of such cellular constituents in the responders versus the nonresponder biological samples. For example, a particular cellular constituent could be more or less abundance in the responders than in the nonresponders. In some embodiments, such discrimination can be, for example, exhibited by differential presence or absence of one or more genetic markers in the responders versus the nonresponders. For example, a particular genetic marker (e.g., a SNP) may be more prevalent or less prevalent in the responder biological samples versus the nonresponder biological samples.

A determination of responsiveness or nonresponsiveness is application dependent and is typically set forth in clinical trial guidelines. In the case of cancer, nonresponsiveness may be, for example, failure to prevent tumor growth, failure to prevent metastasis, or some other adverse clinical event. In some embodiments, nonresponsiveness may in fact be observation of an unwanted side effect. Thus, for example, the responders may be those biological samples that do not exhibit an undesired side effect (e.g., an allergic reaction or some other adverse clinical event) whereas the responders may be those biological samples that do exhibit the undesired side effect.

Step 210. In step 210, a discriminating set of cellular constituents in the first plurality of cellular constituents is identified, where the measurements in the second plurality of molecular profiles for each respective cellular constituent in the discriminating set of cellular constituents discriminates between the responder set of biological samples and the nonresponder set of biological samples. In some embodiments, a cellular constituent in the discriminating set of cellular constituents is a nucleic acid or a protein. In some embodiments, measurements for a cellular constituent in the set of discriminating set of cellular constituents discriminates with a p value of less than 0.1, less than 0.8, less than 0.7, less than 0.05, less than 0.03, less than 0.01, or less than 0.005 as determined by a parametric or nonparametric test using measurements for the cellular constituent in the molecular profiles of the responder set of biological samples and measurements for the cellular constituent in the molecular profiles of the nonresponder set of biological samples. In some embodiments the test is a nonparametric test (e.g., a Chi-square test, a Phi coefficient, Wilcoxon rank sum test, a Fisher exact test, etc.). In some embodiments, the test is a parametric test (e.g., analysis of variance or a t-test). In some embodiments, the test is a t-test, a paired t-test, analysis of variance (ANOVA), a repeated measures ANOVA, a simple linear regression, a nonlinear regression, a multiple linear regression, a multiple nonlinear regression, a Wilcoxon signed-rank test, a MannWhitney test, a Kruskal-Wallis test, a Friedman test, a Spearman rank order correlation coefficient, a Kendall Tau analysis, or a nonparametric regression test. See, e.g., Snedecor and Cochran, 1985, *Statistical Methods*, Iowa State University Press, Ames, Iowa; Agresti, An Introduction to Categorical Data Analysis, John Wiley & Sons, Inc., 1996, New York; Duda et al., *Pattern Classification*, 2001, John Wiley & Sons. New York; Smith, *Statistical Reasoning*, 1985, Allyn and Bacon, Needham Heights, Mass., each of which is hereby incorporated by reference in its entirety.

In the Analysis of Variance (ANOVA) method (see, e.g., *Statistics for Experimenters*, by Box, Hunter and Hunter, John Wiley & Sons, 1978) cellular constituent abundance data analysis is used to determine differential abundance between responders and nonresponders. In a one-way ANOVA, there is one experimental factor under investigation (responder versus nonresponder). The goal is to find out from measured data whether a cellular constituent discriminates the experimental factor. In a two-way ANOVA, there are two factors under investigation, for example, drug effect and dosage effect on response. Each factor may have multiple levels. Interaction between the two factors is also included in the ANOVA analysis. All such ANOVA methods are within the scope of the present invention.

A Wilcoxon rank sum test tests if two pluralities of measurements are identical (see, e.g., Snedecor and Cochran, Statistical Methods, Eighth Edition, 1989, Iowa State University Press, pp. 142-144; McClave and Sincich, 2002, Statistics, Ninth Edition, Prentice Hall, Chapter 14). The Wilcoxon rank sum test can be considered a non-parametric equivalent of the unpaired t-test. It is used to test the hypothesis that two independent samples have come from the same population. Because it is non-parametric, it makes only limited assumptions about the distribution of the data. It assumes that the shape of the distribution is similar in the two groups.

In some embodiments, the discriminating set of cellular constituents comprises 2 or more cellular constituents, 10 or more cellular constituents, 20 or more cellular constituents, 30 or more cellular constituents, 40 or more cellular constituents, 50 or more cellular constituents, between 20 and 100 cellular constituents, between 10 and 1000 cellular constituents, and/or less than 200 cellular constituents.

In some embodiments, a cellular constituent discriminates between the responder set of biological samples ("responders") and the nonresponder set of biological samples ("nonresponders") because it exhibits a differential abundance in the responders versus nonrepsonders. For example, a particular cellular constituent may be more abundant in the responders versus the nonresponders. The statistical tests described above can be used to determine whether such a differential abundance exists. For example, a t-test can be used to determine whether the abundance of a particular cellular constituent discriminates between the responders and the nonresponders. A particular p value for the t-test can be chosen as the threshold for determining whether the cellular constituent discriminates between responders and nonresponders. For instance, of the p value for the t-test (or other form of statistical test such as the ones described above) is 0.05 or less, the cellular constituent is deemed to discriminate between responders and nonresponders in some embodiments of the present invention.

In some embodiments, a cellular constituent discriminates between the responder set of biological samples ("responders") and the nonresponder set of biological samples ("nonresponders") because it contains one or more genetic markers that are differentially present in the responders versus the nonrepsonders. In some embodiments, a cellular constituent is, in fact, a site on a genome that is characterized by one or more genetic markers. Such genetic markers include, but are not limited to, single nucleotide polymorphisms (SNPs), SNP haplotypes, microsatellite markers, restriction fragment length polymorphisms (RFLPs), short tandem repeats, sequence length polymorphisms, DNA methylation, random amplified polymorphic DNA (RAPD), amplified fragment length polymorphisms (AFLP), and "simple sequence repeats." For more information on molecular marker methods, see generally, *The DNA Revolution* by Andrew H. Paterson 1996 (Chapter 2) in: *Genome Mapping in Plants* (ed. Andrew H. Paterson) by Academic Press/R. G. Landis Company, Austin, Tex., 7-21, which is hereby incorporated by reference herein in its entirety. For example, a particular cellular constituent may contain one or more genetic marker that are more often present in the responders versus the nonresponders. The statistical tests described above can be used to determine whether such a differential presence of genetic markers exists. For example, a t-test can be used to determine whether the prevalence of one or more genetic markers in a cellular constituent discriminates between the responders and the nonresponders. A particular p value for the t-test can be chosen as the threshold for determining whether the cellular constituent discriminates between responders and nonresponders. For instance, of the p value for the t-test (or other form of statistical test such as the ones described above) is 0.05 or less, the cellular constituent is deemed to discriminate between responders and nonresponders in some embodiments of the present invention based on differential presence or absence of one or more genetic markers within the cellular constituent.

Step 212. In step 212, a candidate set of molecular profiles in the stored first plurality of molecular profiles is identified that have measurements for the discriminating set of cellular constituents that match the measurements of the discriminating set of cellular constituents in the responder set of biological samples. In this way, a plurality of subjects for the clinical trial is identified from those subjects from which the candidate set of molecular profiles were derived. Various techniques can be used to determine whether a molecular profile in the stored first plurality of molecular profiles has measurements for the discriminating set of cellular constituents that match the measurements of the discriminating set of cellular constituents in the responder set of biological samples. For example, the responder set of biological samples and the nonresponder set of biological samples can be used to train a classifier. Thus, the responder set of biological samples and the nonresponder set of biological samples collectively can be considered a training population. The classifier can then be used to determine which of the molecular profiles in the stored first plurality of molecular profiles match the responder set of biological samples. For instance, a molecular profile in the stored first plurality of molecular profiles matches the responder set of biological samples when a classifier trained on the above described training population returns a p value of less than 0.2, less than 0.1, less than 0.05, or less than 0.0 for the molecular profile.

In some embodiments a first molecular profile in a stored first plurality of molecular profiles is deemed to have measurements for a discriminating set of cellular constituents that match the measurements of the discriminating set of cellular constituents in the responder set of biological samples when a metric between (i) the measurements for the discriminating set of cellular constituents in the first molecular profile and (ii) the measurements for the discriminating set of cellular constituents in the responder set of biological samples exceeds a threshold value. In some embodiments the metric is a correlation coefficient computed between (i) the measurements for the discriminating set of cellular constituents in the first molecular profile and (ii) the measurements for the discriminating set of cellular constituents in the responder set of biological samples and the threshold value is a correlation coefficient of at least 0.3, at least 0.4, at least 0.5, at least 0.6, at least 0.7, at least 0.8, at least 0.9, or at least 0.95.

In some embodiments, the measurements for a discriminating set of cellular constituents comprise a determination of the presence or absence of genetic markers. Thus, two molecular profiles that comprise such a determination of the presence or absence of genetic markers are said to "match" when they are determined to have the same genetic markers. In some embodiments, a classifier is used to classify molecular profiles as responders and nonresponders based on the absence or presence of genetic markers. In such an approach, the responder set of biological samples and the nonresponder set of biological samples collectively can be considered a training population. A classifier is developed from this training population based on the differential presence or absence of genetic markers in the responders and nonresponders of the training population. The classifier can then be used to determine which of the molecular profiles in the stored first plurality of molecular profiles match the responder set of biological samples based on presence or absence of genetic markers. For instance, a molecular profile in the stored first plurality of molecular profiles matches the responder set of biological samples when a classifier trained on the above described training population returns a p value of less than 0.2, less than 0.1, less than 0.05, or less than 0.0 for the molecular profile.

In one embodiment, comparison of a biomarker profile in the first plurality of biomarker profiles to biomarker profiles obtained from the training population is performed, and comprises applying a decision rule. The decision rule is constructed using a data analysis algorithm, such as a computer pattern recognition algorithm. Other suitable data analysis algorithms for constructing decision rules include, but are not limited to, logistic regression or a nonparametric algorithm that detects differences in the distribution of feature values (e.g., a Wilcoxon Signed Rank Test (unadjusted and adjusted)). The decision rule can be based upon measurement values for two, three, four, five, 10, 20 or more discriminating cellular constituents. Such measurements can be cellular constituent abundance values, absence or presence of genetic markers in the discriminating set of cellular constituents, or some other form of measurement. In one embodiment, the decision rule is based on hundreds of discriminating cellular constituents or more. Decision rules may also be built using a classification tree algorithm. For example, each biomarker profile from the training population can comprise at least three features, where the features are predictors in a classification tree algorithm. The decision rule predicts membership within a class (e.g., membership in the responder class or nonresponder class) with an accuracy of at least about at least about 70%, of at least about 75%, of at least about 80%, of at least about 85%, of at least about 90%, of at least about 95%, of at least about 97%, of at least about 98%, of at least about 99%, or about 100%.

Suitable data analysis algorithms are known in the art, some of which are reviewed in Hastie et al., supra. In a specific embodiment, a data analysis algorithm of the invention comprises Classification and Regression Tree (CART), Multiple Additive Regression Tree (MART), Prediction Analysis for Microarrays (PAM) or Random Forest analysis. Such algorithms classify complex spectra from biological materials, such as a blood sample, to distinguish subjects as normal or as possessing biomarker expression levels characteristic of a particular disease state. In other embodiments, a data analysis algorithm of the invention comprises ANOVA and nonparametric equivalents, linear discriminant analysis, logistic regression analysis, nearest neighbor classifier analysis, neural networks, principal component analysis, quadratic discriminant analysis, regression classifiers, and support vector machines. While such algorithms may be used to construct a decision rule and/or increase the speed and efficiency of the application of the decision rule and to avoid investigator bias, one of ordinary skill in the art will realize that computer-based algorithms are not required to carry out the methods of the present invention. Exemplary data analysis algorithms that can be used to identify molecular profiles in the first plurality of molecular profiles that match the molecular profiles in the responder set of biological samples are described in Section 5.11, below.

Decision rules can be used to evaluate molecular profiles, regardless of the method that was used to generate the biomarker profile. For example, suitable decision rules that can be used to evaluate molecular profiles generated using gas chromatography, as discussed in Harper, "Pyrolysis and GC in Polymer Analysis," Dekker, New York (1985). Further, Wagner et al., 2002, *Anal. Chem.* 74:1824-1835 disclose a decision rule that improves the ability to classify subjects based on spectra obtained by static time-of-flight secondary ion mass spectrometry (TOF-SIMS). Additionally, Bright et al., 2002, *J. Microbiol. Methods* 48:127-38, hereby incorporated by reference herein in its entirety, disclose a method of distinguishing between bacterial strains with high certainty (79-89% correct classification rates) by analysis of MALDI-TOF-MS spectra. Dalluge, 2000, *Fresenius J. Anal. Chem.* 366: 701-711, hereby incorporated by reference herein in its entirety, discusses the use of MALDI-TOF-MS and liquid chromatography-electrospray ionization mass spectrometry (LC/ESI-MS) to classify profiles of biomarkers in complex biological samples. Thus, the molecular profiles of the present invention are not limited to microarray data.

In some embodiments, the candidate set of molecular profiles comprises 10 or more molecular profiles, 100 or more molecular profiles, 200 or more molecular profiles, 300 or more molecular profiles, between 50 and 500 molecular profiles, between 10 and 1000 molecular profiles, or less than 10,000 molecular profiles. In typical embodiments, each of these molecular profiles represents a different subject in the first plurality of subjects. However, in some embodiments, one or more of the molecular profiles in the candidate set of molecular profiles are measurements of different biological samples taken from the same subject.

Step 214. The preceding steps identify a plurality of subjects for the clinical trial. This is highly advantageous because such subjects are more likely to be responsive to the therapy of interest. In step 214, the therapy of interest is administered to the plurality of subjects identified in step 212.

Step 216. In step 216, a first set of subjects in the plurality of subjects that are responders to the therapy of interest and a second set of subjects in the plurality of subjects that are not responders to the therapy of interest are identified. As in step 208, a determination of responsiveness or nonresponsiveness is application dependent and is typically set forth in clinical trial guidelines. In the case of cancer, nonresponsiveness may be, for example, failure to prevent tumor growth, failure to prevent metastasis, or some other adverse clinical event. In some embodiments, nonresponsiveness may in fact be observation of an unwanted side effect. Thus, for example, the responders may be those biological samples that do not exhibit an undesired side effect (e.g., an allergic reaction or some other adverse clinical event) whereas the responders may be those biological samples that do exhibit the undesired side effect.

Step 218. In step 218, a revised set of discriminating cellular constituents is identified whose measurement values taken from the plurality of subjects prior to exposure to the therapy of interest discriminates between the first set of subjects in the plurality of subjects identified in step 216 that are responders to the therapy of interest and the second set of subjects in the plurality of subjects identified in step 216 that are not responders to the therapy of interest. Thus, step 218 serves to refine the set of cellular constituents identified in step 210. In fact, however, it is possible for their to be no cellular constituents in the revised set of discriminating cellular constituents of step 218 that are also in the set of discriminating cellular constituents of step 210. More typically, there are cellular constituent common to the set of discriminating cellular constituents of step 210 and the revised set of discriminating cellular constituents of step 218.

In some embodiments, the revised set of discriminating cellular constituents comprises 2 or more cellular constituents, 10 or more cellular constituents, 20 or more cellular constituents, 30 or more cellular constituents, 40 or more cellular constituents, 50 or more cellular constituents, between 20 and 100 cellular constituents, between 10 and 1000 cellular constituents, and/or less than 200 cellular constituents.

Step 220. In step 220, a new plurality of subjects is identified for the clinical trial for the therapy of interest based on matches between cellular constituent values for the revised set of discriminating cellular constituents of step 218 in (i) the molecular profiles of the first set of subjects in the plurality of subjects that are responders to the therapy of interest and (ii) the molecular profiles of the first plurality of subjects. Various techniques can be used to determine whether a molecular profile of the first set of subjects in the plurality of subjects that are responders to the therapy of interest have measurements for the revised set of discriminating cellular constituents that match the measurements of the discriminating set of cellular constituents in the molecular profiles of the first plurality of subjects. For example, the first and second sets of step 216 can be used to train a classifier. Thus, the first and second sets of subjects of step 216 collectively can be considered a training population. The classifier can then be used to determine which of the molecular profiles in the stored first plurality of molecular profiles match the responder set of biological samples. In one embodiment, such comparisons comprise applying a decision rule. The decision rule is constructed using a data analysis algorithm, such as a computer pattern recognition algorithm (classifier). The use of such classifiers is discussed in conjunction with step 212 above and Section 5.11, below. As noted in FIG. 2B, steps 214, 216, 218, and 220 can be repeated a number of times in an iterative fashion in order to identify suitable subjects for a therapy of interest. In some embodiments, these steps are repeated two times, three times, four times, five times, six times, more than 10 times, between 2 and 12 times, or less than five times.

5.4. Methods for Obtaining Patient Information

As noted above, patient records 46 can optionally further include patient information 62. In some embodiments, such patient information is entered using a patient information data entry module. In some embodiments, the patient information is an address where the subject lives, next of kin contact information, a telephone number for the subject, an age of the subject, an allergy of the subject, a height of the subject, a weight of the subject, a race of the subject, insurance information for the subject, subject treatment history, a diagnosis of the subject, or family medical history for the subject. In some embodiments, the patient information is entered directly onto a web-based questionnaire. Such a web-based questionnaire can be served, for example, by patient information data entry module 78 (FIG. 1).

In some embodiments, the molecular profile for the subject is in the candidate set of molecular profiles identified in step in step 212, above. Further, the molecular profile from the candidate set is removed when the patient information does not satisfy a selection criterion and, correspondingly, the molecular profile is retained in the candidate set when the patient information satisfies the selection criterion. Representative nonlimiting examples of a selection criterion include, but are not limited to, a minimum age, a maximum age, a minimum weight, or a maximum weight.

The used of a web-based questionnaire is highly advantageous. Using such an approach, patient information is entered directly into a computer without risk of loss of paper errors or clerical data entry errors that may arise when such paper records are eventually entered into a computer. Furthermore, the web-based questionnaire can be filled out at a remote site and the information sent to a central computer, such as computer 10 of FIG. 1, by electronic means. FIG. 5 illustrates information that can be provided by a surgeon following surgery. Such information can be used to identify and/or find subjects that are suitable for a clinical trial. In FIG. 5, AWOD stands for "alive without disease" and AWD stands for "alive with the disease." FIG. 6 illustrates information that can be provided by a medical oncologist following treatment. Such information can also be used to identify and/or find subjects that are suitable for a clinical trial.

In some embodiments, patient information for patients represented in patient database 44 (FIG. 1) is acquired throughout the patient lifetimes, at least once annually. In some embodiments, the existing staff of a medical institution (e.g., nurses) is enlisted as much as possible for this purpose, using data managers to audit, monitor the data, and seek out patient data when points are "lost to follow up". The data managers can track down the patient who go and see other doctors rather than their originating doc. They can also seek out data from cancer registries. One purpose of such efforts is to determine what drug therapies the patient has received (and thus can be associated with the gene expression profile from the biological sample accessed), and if there has been any progression of disease. In some embodiments responses to therapy are also recorded for many if not all of the subjects represented by patient database 44. In other embodiments, responses to therapy are only recorded for those patients on therapeutic trials.

In some embodiments a molecular profile is removed from the candidate set of molecular profiles when the patient information for the subject from which the molecular profile was constructed does not satisfy a selection criterion. Molecular profiles in the candidate set are retained in the candidate set when the patient information satisfies the selection criterion. Exemplary selection criterion include, but are not limited to, a minimum age, a maximum age, a minimum weight, or a maximum weight.

5.5. Follow Up

In some embodiments a molecular profile is removed from the candidate set of molecular profiles when the patient information for the subject from which the molecular profile was constructed, that is collected as described in this section, does not satisfy a selection criterion. Molecular profiles in the candidate set are retained in the candidate set when the patient information satisfies the selection criterion. Exemplary selection criterion include, but are not limited to, a minimum age, a maximum age, a minimum weight, or a maximum weight. Furthermore, the information collected in this section can be used to refine the population that is considered responders versus nonresponders. For instance, longitudinal data collected in this section can be used to determine those subjects that are responders versus nonresponders as a function of time to a therapy of interest. Thus, the techniques in this section, for example, help to determine responders versus nonresponders in step 206 described above. Furthermore, in some embodiments, subjects, from which information is obtained as described in this section, can be the originators of the "second plurality" of biological samples described in step 206 above. As such, the techniques in this section provide innovative ways to collect the molecular profiles, patient information, and/or clinical features needed to define a responder set and a nonresponder set of biological samples in accordance with some embodiments of the present invention.

In some embodiments, subject progression free survival data is recorded for subjects represented by patient database 44. In such embodiments, medical practitioners (e.g., nurses) record progression of disease since it is generally not in dispute. FIG. 7 illustrates a mock up of two forms that medical practitioners can fill out during follow up. In some embodiments, the forms are in the form of a web-based question are. The forms are designed to be simple so that the medical practitioner can fill them out at a medical doctor's direction in a short period of time. In one approach, at beginning of the clinic day, a medical practitioner sends a batch query of medical records to computer 10 (FIG. 1) to see what patients for the day would have already been permitted to medical treatment, and now are in the follow up period with their doctor. In this scenario, a new patient seeing a medical oncologist for the first time would not be in the database, but would be referred for a biopsy, and at that moment in time would be in the database. The medical oncologist would order a biopsy of the suspicious lesion and the patient would then come back to the office for follow up. At this first follow up visit, the nurse would be notified the patient is in on the premises and a "metastatic" follow-up form (FIG. 7A) would need to be completed. In some embodiments, this form would be a web-based questionnaire or other form of electronic record (e.g., a Cerner record). In some embodiments, a particular LOGO would appear up on the title bar of the web-based questionnaire or Cerner record. This would trigger the medical practitioner to fill out an annual record. In some embodiments, the logo is followed by the months of follow-up the patient is currently in so the nurses can determine if a follow-up form needs to be completed. The medical practitioner receives back a list of consented, established patients for the day and now knows on which patient a follow up form needs to be completed. In some embodiments, the software that drives such forms in configures such that only patients due for their annual follow-up would need to have data entered thereby significantly reducing the burden on the medical practitioner. However, in other embodiments, the forms are not filtered on such a basis on the premise that multiple entries provides security to the answers. In some embodiments, the medical practitioner opts to take notes as the day proceeds or enter patients in real time over the web. In other embodiments, the medical practitioner can provide filled forms by FAX/SCAN as well as, preferably, web entry. FIG. 7B illustrates a similar type of form that is appropriate for follow-up following a primary resection.

Once a patient has been assigned a treatment regimen, the clinical outcome of the patient over time is periodically monitored in some embodiments. The frequency with which a patient is monitored will vary and is generally determined by the patient diagnosis. In some embodiments, the patient is monitored almost continuously. In other embodiments, the patient is monitored once a year, once a month, weekly, or daily. Optionally, a biological sample is obtained from the patient during each monitoring instance. The biological sample can be, for example, a blood sample, a tissue sample, or a tumor sample. A molecular profile of each successive biological sample is preferably made. FIG. 8 illustrates a data structure 610 in which each of the successive molecular profiles can be stored. The data structure includes an identity of a plurality of a plurality of cellular constituents 802. In one embodiment, each cellular constituent is a human gene and each identifier 802 uniquely identifies a human gene. For each identified cellular constituents, there is an array 804 for storing the abundance level of the cellular constituent at various time points. For instance, record 804-1-1 stores the abundance level of the corresponding cellular constituent at a first time point, record 804-1-2 stores the abundance level of the corresponding cellular constituent at a second time point, and so forth.

5.6. Exemplary Normalization Routines

A number of different normalization protocols can be used to normalize cellular constituent abundance data. Some such normalization protocols are described in this section. Typically, the normalization comprises normalizing the expression level measurement of each gene in a plurality of genes that is expressed by patient. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$Z\text{-score}_{ij} = (I_{ij} - mnI_i)/sdI_i,$$

and $$Zdiff_j(x,y) = Z\text{-score}_{xj} - Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (median$I_i$) for all of the spots in that sample. Thus, upon normalization by the median intensity normalization method, the raw intensity $I_{ij}$ for probe i and spot j, has the value $Im_{ij}$ where, $$Im_{ij} = (I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (median$I_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value $Im_{ij}$ where, $$Im_{ij}=\log(1.0+(I_{ij}/medianI_i)).$$

Yet another normalization protocol is the Z-score standard deviation log of intensity protocol. In this protocol, raw expression intensities are normalized by the mean log intensity ($mnLI_i$) and standard deviation log intensity ($sdLI_i$). For microarray data, the mean log intensity and the standard deviation log intensity is computed for the log of raw intensity of control genes. Then, the Z-score intensity $ZlogS_{ij}$ for probe i and spot j is:

$$Z\log S_{ij}=(\log(I_{ij})-mnLI_i)/sdLI_i.$$

Still another normalization protocol is the Z-score mean absolute deviation of log intensity protocol. In this protocol, raw expression intensities are normalized by the Z-score of the log intensity using the equation (log(intensity)−mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity $mnLI_i$ and the mean absolute deviation log intensity $madLI_i$ are computed for the log of raw intensity of control genes. Then, the Z-score intensity $ZlogA_{ij}$ for probe i and spot j is:

$$Z\log A_{ij}=(\log(I_{ij})-mnLI_i)/madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. See, for example, section 5.8.1.5. In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5−medianBkgdCy5)/(medianCy3−medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

5.7. Analytic Kit Implementation

In one embodiment, the methods of this invention can be implemented by use of kits. Such kits contain microarrays, such as those described in subsections below. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In a particular embodiment, the probes contained in the kits of this invention are nucleic acids capable of hybridizing specifically to nucleic acid sequences derived from RNA species in cells collected from an organism of interest.

In a preferred embodiment, a kit of the invention also contains one or more databases described above, encoded on computer readable medium, and/or an access authorization to use the databases described above from a remote networked computer.

In another preferred embodiment, a kit of the invention further contains software capable of being loaded into the memory of a computer system such as the one described above. The software contained in the kit of this invention, is essentially identical to the software described above.

Alternative kits for implementing the analytic methods of this invention will be apparent to one of skill in the art and are intended to be comprehended within the accompanying claims.

5.8. Transcriptional State Measurements

This section provides some exemplary methods for measuring the expression level of genes, which are one type of cellular constituent. One of skill in the art will appreciate that this invention is not limited to the following specific methods for measuring the expression level of genes in each organism in a plurality of organisms.

5.8.1. Transcript Assay Using Microarrays

Nucleic acid microarrays exploit a phenomenon known as base-pairing or hybridization. To form the array, genetic samples are arranged in an orderly manner, typically in a rectangular grid, on a substrate. Examples of commonly used substrates include microplates and blotting membranes. Many modern microarrays include an array of oligonucleotide or peptide nucleic acid (PNA) probes, and the array is synthesized either in situ (on-chip) or by conventional synthesis followed by on-chip immobilization. The array on the chip is exposed to labeled sample DNA, hybridized, and the identity/abundance of complementary sequences is determined.

One use of nucleic acid microarray technology involves identification of the gene sequence. Another use of nucleic acid microarray technology involves determination of expression level of genes, generally referred to as the abundance of the genes. In particular, expression or abundance of a gene is a measure of a relative level of activity of the gene in replication or translation in the presence of the probe. Microarrays have been used for a number of beneficial purposes including, for example, identifying biomarkers of cancer (Welsh et al., 2003, *Proc. Natl. Acad. Sci. USA* 100:3410-3415), creating gene expression-based classifications of cancers (Alzadeh et al., 2000, *Nature* 403:513-11; and Garber et al., 2001, *Proc. Natl. Acad. Sci. USA* 98:13784-13789), and in drug discovery (Marton et al., 1998, *Nat. Med.* 4:1293-1301; and Gray et al., 1998, *Science* 281:533-538).

The techniques described in this section are particularly useful for the determination of the expression state or the transcriptional state of a cell or cell type or any other cell sample by monitoring expression profiles. These techniques include the provision of polynucleotide probe arrays that can be used to provide simultaneous determination of the expression levels of a plurality of genes. These techniques further provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance ratios. Preferably, measurement of the expression profile is made by hybridization to transcript arrays. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

In one embodiment, a molecular profile is an expression profile that is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. Microarrays are preferably small, e.g., between 1 cm$^2$ and 500 cm$^2$, preferably 1 to 100 cm$^2$. However, both larger and smaller arrays are also contemplated and may be preferable, e.g., for simultaneously evaluating a very large number or very small number of different probes.

Preferably, a given binding site or unique set of binding sites in the microarray will specifically bind (e.g., hybridize) to a nucleotide sequence in a single gene from a cell or organism (e.g., a specific mRNA or a specific cDNA derived therefrom). In some embodiments, the microarray is an Affymetrix (Santa Clara, Calif.) human genome U133 set. The Human Genome U133 (HG-U133) set, consisting of two GeneChip® arrays, contains almost 45,000 probe sets representing more than 39,000 transcripts derived from approximately 33,000 well-substantiated human genes. This set design uses sequences selected from GenBank®, dbEST, and RefSeq.

The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (e.g., the sequence) of each probe can be determined from its position on the array (e.g., on the support or surface). In some embodiments, the arrays are ordered arrays.

Preferably, the density of probes on a microarray or a set of microarrays is 100 different (e.g., non-identical) probes per 1 cm$^2$ or higher. More preferably, a microarray used in the methods of the invention will have at least 550 probes per 1 cm$^2$, at least 1,000 probes per 1 cm$^2$, at least 1,500 probes per 1 cm$^2$ or at least 3,000 probes per 1 cm$^2$. In a particularly preferred embodiment, the microarray is a high density array, preferably having a density of at least 2,500 different probes per 1 cm$^2$. The microarrays used in the invention therefore preferably contain at least 2,500, at least 5,000, at least 10,000, at least 15,000, at least 20,000, at least 25,000, at least 50,000 or at least 55,000 different (e.g., non-identical) probes.

In one embodiment, the microarray is an array (e.g., a matrix) in which each position represents a discrete binding site for a nucleotide sequence of a transcript encoded by a gene (e.g., for an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment.

In some embodiments of the present invention, a gene is represented in the profiling arrays by a set of binding sites comprising probes with different polynucleotides that are complementary to different sequence segments of the gene. Such polynucleotides are preferably of the length of 15 to 200 bases, more preferably of the length of 20 to 100 bases, most preferably 40-60 bases. Each probe sequence can also comprise linker sequences in addition to the sequence that is complementary to its target sequence. As used herein, a linker sequence is a sequence between the sequence that is complementary to its target sequence and the surface of support. For example, in preferred embodiments, the profiling arrays of the invention comprise one probe specific to each target gene. However, if desired, the profiling arrays can contain at least 2, 5, 10, 100, or 1000 or more probes specific to some target genes. For example, the array can contain probes tiled across the sequence of the longest mRNA isoform of a gene at single base steps.

The use of a two-color fluorescence labeling and detection scheme to define alterations in gene expression has been described in connection with detection of mRNAs, e.g., in Shena et al., 1995, *Science* 270:467-470, which is incorporated by reference herein in its entirety for all purposes. An advantage of using cDNA labeled with two different fluorophores is that a direct and internally controlled comparison of the mRNA expression levels corresponding to each arrayed gene in two cell states can be made, and variations due to minor differences in experimental conditions (e.g., hybridization conditions) will not affect subsequent analyses. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5Ncarboxy-fluorescein ("FMA"), 2N,7N-dimethoxy-4N, 5N-dichloro-6-carboxy-fluorescein ("JOE"), N,N,NN,NN-tetramethyl-6-carboxy-rhodamine ("TAMRA"), 6Ncarboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (e.g., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments in which polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual,* 2nd ed., Vol. 1-3, Cold Spring Harbor Laboratory, Cold Spring Harbor, N.Y., which is hereby incorporated by reference herein in its entirety).

5.8.1.1. Preparing Probes for Microarrays

As noted above, the "probe" to which a particular polynucleotide molecule specifically hybridizes according to the invention is a complementary polynucleotide sequence. Preferably one or more probes are selected for each target gene. For example, when a minimum number of probes are to be used for the detection of a gene, the probes normally comprise nucleotide sequences greater than 10 bases in length, greater than 20 bases in length, greater than 30 bases in length, or greater than 40 bases in length. Alternatively, when a large set of redundant probes is to be used for a gene, the probes normally comprise nucleotide sequences of 40-60 bases.

An alternative, means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14, 5399-5407; McBride et al., 1983, *Tetrahedron Lett.* 24, 246-248). Synthetic sequences are typically between 15 and 600 bases in length, more typically between 20 and 100 bases, most preferably between 40 and 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363, 566-568; and U.S. Pat. No. 5,539,083). In alternative embodiments, the hybridization sites (e.g., the probes) are made from plasmid or phage clones of genes, cDNAs (e.g., expressed sequence tags), or inserts therefrom (Nguyen et al., 1995, *Genomics* 29:207-209).

5.8.1.2. Attaching Nucleic Acids to the Solid Surgace

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material. One method for attaching the nucleic acids to a surface is by printing on glass plates, as is described generally by Schena et al, 1995, Science 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

Another method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per gene.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic* Engineering 20, Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3N end of the polynucleotide. Alternatively, polynucleotide probes can be attached to the surface covalently at the 5N end of the polynucleotide (see for example, Blanchard, 1998, in Synthetic DNA Arrays in Genetic Engineering 20, J. K. Setlow, Ed., Plenum Press, New York at pages 111-123).

5.8.1.3. Target Polynucleotide Molecules

Target polynucleotides that can be analyzed by the methods and compositions of the invention include RNA molecules such as, but by no means limited to, messenger RNA (mRNA) molecules, ribosomal RNA (rRNA) molecules, cRNA molecules (i.e., RNA molecules prepared from cDNA molecules that are transcribed in vivo) and fragments thereof.

Target polynucleotides that can also be analyzed by the methods of the present invention include, but are not limited to DNA molecules such as genomic DNA molecules, cDNA molecules, and fragments thereof including oligonucleotides, ESTs, STSs, etc.

The target polynucleotides can be from any source. For example, the target polynucleotide molecules can be naturally occurring nucleic acid molecules such as genomic or extragenomic DNA molecules isolated from a patient, or RNA molecules, such as mRNA molecules, isolated from a patient. Alternatively, the polynucleotide molecules can be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, the target polynucleotides can correspond to particular fragments of a gene transcript. For example, the target polynucleotides may correspond to different exons of the same gene, e.g., so that different splice variants of the gene can be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891, 636, 5,716,785; 5,545,522 and 6,132,997; see also, U.S. Pat. No. 6,271,002, and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleotides are short and/or fragmented polynucleotide molecules that are representative of the original nucleic acid population of the cell.

The target polynucleotides to be analyzed by the methods of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5Ncarboxy-fluorescein ("FMA"), 2N,7N-dimethoxy-4N,5N-dichloro-6-carboxy-fluorescein ("JOE"), N,N,NN,NN-tetramethyl-6-carboxy-rhodamine ("TAMRA"), 6Ncarboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.8.1.4. Hybridization to Microarrays

As described supra, nucleic acid hybridization and wash conditions are chosen so that the polynucleotide molecules to be analyzed by the invention (referred to herein as the "target polynucleotide molecules") specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (e.g., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2%

SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, *Nonisotopic DNA Probe Techniques*, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.8.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (e.g., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, *Science* 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, can be used to monitor mRNA abundance levels at a large number of sites simultaneously.

Signals are recorded and, in a preferred embodiment, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors can be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (e.g., the abundance is different in the two sources of mRNA tested) or as not perturbed (e.g., the relative abundance is the same). As used herein, a difference between the two sources of RNA of at least a factor of 25% (e.g., RNA is 25% more abundant in one source than in the other source), more usually 50%, even more often by a factor of 2 (e.g., twice as abundant), 3 (three times as abundant), or 5 (five times as abundant) is scored as a perturbation. Present detection methods allow reliable detection of differences of an order of 1.5 fold to 3-fold.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.8.2. Other Methods of Transcriptional State Measurement

The transcriptional state of cellular constituent in a biological specimen can be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. USA 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, Science 270: 484-487).

RT-PCR. In certain embodiments, the level of expression of one or more genes is measured by amplifying RNA from a sample using reverse transcription (RT) in combination with the polymerase chain reaction (PCR). In accordance with this embodiment, the reverse transcription may be quantitative or semi-quantitative. The RT-PCR methods taught herein may be used in conjunction with the microarray methods described above. For example, a bulk PCR reaction may be performed, the PCR products may be resolved and used as probe spots on a microarray.

Total RNA, or mRNA from a sample is used as a template and a primer specific to the transcribed portion of the gene(s) is used to initiate reverse transcription. Methods of reverse transcribing RNA into cDNA are well known and described in Sambrook et al., 2001, supra. Primer design can be accomplished based on known nucleotide sequences that have been published or available from any publicly available sequence database such as GenBank. For example, primers may be designed for any of the genes that are determined to be discriminating between responders and nonresponders. Further, primer design may be accomplished by utilizing commercially available software (e.g., Primer Designer 1.0, Scientific Software etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts. The method of PCR is well known in the art. PCR, is performed, for example, as described in Mullis and Faloona, 1987, Methods Enzymol. 155:335, which is hereby incorporated herein by reference in its entirety.

PCR can be performed using template DNA or cDNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of 10 M PCR buffer 1 (Perkin-Elmer, Foster City, Calif.), 0.4 µl of 1.25 M dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Quantitative RT-PCR ("QRT-PCR"), which is quantitative in nature, can also be performed to provide a quantitative measure of gene expression levels. In QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.) or as provided by Applied Biosystems (Foster City, Calif.) is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96-well plates so that samples derived from many individuals are processed and measured simultaneously. The Taqman system has the additional advantage of not requiring gel electrophoresis and allows for quantification when used with a standard curve.

A second technique useful for detecting PCR products quantitatively is to use an intercalating dye such as the commercially available QuantiTect SYBR Green PCR (Qiagen, Valencia Calif.). RT-PCR is performed using SYBR green as a fluorescent label which is incorporated into the PCR product during the PCR stage and produces a flourescense proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the fluorescence increases giving a quantitative measurement of gene expression.

Additional techniques to quantitatively measure RNA expression include, but are not limited to, polymerase chain reaction, ligase chain reaction, Qbeta replicase (see, e.g., International Application No. PCT/US87/00880, which is hereby incorporated by reference), isothermal amplification method (see, e.g., Walker et al., 1992, *Proc. Natl. Acad. Sci. USA* 89:382-396, which is hereby incorporated herein by reference), strand displacement amplification (SDA), repair chain reaction, Asymmetric Quantitative PCR (see, e.g., U.S. Publication No. US 2003/30134307A1, herein incorporated by reference) and the multiplex microsphere bead assay described in Fuja et al., 2004, *Journal of Biotechnology* 108: 193-205, herein incorporated by reference.

The level of expression of one or more discriminating genes can, for example, be measured by amplifying RNA from a sample using amplification (NASBA). See, e.g., Kwoh et al., 1989, *Proc. Natl. Acad. Sci. USA* 86:1173; International Publication No. WO 88/10315; and U.S. Pat. No. 6,329,179, each of which is hereby incorporated by reference. In NASBA, the nucleic acids may be prepared for amplification using conventional methods, e.g., phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques may be used to separate amplification products. For example, amplification products may be separated by agarose, agarose-acrylamide or polyacrylamide gel electrophoresis using conventional methods. See Sambrook et al., 2001. Several techniques for detecting PCR products quantitatively without electrophoresis may also be used according to the invention (see, e.g., *PCR Protocols, A Guide to Methods and Applications*, Innis et al., 1990, Academic Press, Inc. N.Y., which is hereby incorporated by reference). For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982, which is hereby incorporated by reference).

Another example of a separation methodology is to covalently label the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by Raggio Italgene (under the C-Track tradename.

Amplification products should be visualized in order to confirm amplification of the nucleic acid sequences of interest, i.e., nucleic acid sequences of one or more of the discriminating genes identified by the methods disclosed herein. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified nucleic acid sequence of interest, i.e., nucleic acid sequences of one or more of the discriminating genes identified by the methods described herein. The probe preferably is conjugated to a chromophore but may be radiolabeled. In another embodiment, the probe is conjugated to a binding partner, such as an antibody or biotin, where the other member of the binding pair carries a detectable moiety.

Northern blot assays. Any hybridization technique known to those of skill in the art can be used to measure molecular profiles. In some embodiments, molecular profiles can be measured by Northern blot analysis (to detect and quantify specific RNA molecules). A standard Northern blot assay can be used to ascertain an RNA transcript size, identify alternatively spliced RNA transcripts, and the relative amounts of one or more genes described herein (in particular, mRNA) in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays. In particular embodiments, a molecular profile is measured using nuclease protection assays (including both ribonuclease protection assays and S1 nuclease assays) to detect and quantify specific mRNAs. Such assays are described in, for example, Sambrook et al., 2001, supra. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

5.9. Measurement of Other Aspects of the Biological State

In various embodiments of the present invention, aspects of the biological state other than the transcriptional state, such as the translational state, the activity state, or mixed aspects can be measured. Thus, in such embodiments, cellular constituent data used in molecular profile can include translational state measurements or even protein expression measurements. Details of embodiments in which aspects of the biological state other than the transcriptional state are described in this section.

5.9.1. Translational State Measurements

Measurement of the translational state can be performed according to several methods. For example, whole genome monitoring of protein (e.g., the "proteome,") can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, *Yeast* 12:1519-1533; Lander, 1996, *Science* 274:536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

In specific embodiments of the invention, the molecular profile can be measured by detecting proteins, for example, by detecting the expression product (e.g., a nucleic acid or protein) of one or more discriminating genes identified by the systems and methods described herein, or post-translationally modified, or otherwise modified, or processed forms of such proteins. In a specific embodiment, a molecular profile is generated by detecting and/or analyzing one or more proteins expressed from a discriminating gene identified by the systems and methods disclosed herein using any method known to those skilled in the art for detecting proteins including, but not limited to protein microarray analysis, immunohistochemistry and mass spectrometry.

Standard techniques may be utilized for determining the amount of the protein or proteins of interest present in a sample. For example, standard techniques can be employed using, e.g., immunoassays such as, for example Western blot, immunoprecipitation followed by sodium dodecyl sulfate polyacrylamide gel electrophoresis, (SDS-PAGE), immunocytochemistry, and the like to determine the amount of protein or proteins of interest present in a sample. One exemplary agent for detecting a protein of interest is an antibody capable of specifically binding to a protein of interest, preferably an antibody detectably labeled, either directly or indirectly.

For such detection methods, if desired, a protein from the sample to be analyzed can easily be isolated using techniques which are well known to those of skill in the art. Protein isolation methods can, for example, be such as those described in Harlow and Lane, 1988, *Antibodies: A Laboratory Manual*, Cold Spring Harbor Laboratory Press (Cold Spring Harbor, N.Y.), which is incorporated by reference herein in its entirety.

In certain embodiments, methods of detection of the proteins involves their detection via interaction with a protein-specific antibody. For example, antibodies directed to a protein of interest can be made. Antibodies can be generated utilizing standard techniques well known to those of skill in the art. In specific embodiments, antibodies can be polyclonal, or more preferably, monoclonal. An intact antibody, or an antibody fragment (e.g., scFv, Fab or F(ab')$_2$) can, for example, be used. For example, antibodies, or fragments of antibodies, specific for a protein of interest can be used to quantitatively or qualitatively detect the presence of a protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a biological sample (e.g., a biopsy specimen) from a patient, and applying thereto a labeled antibody that is directed to a protein of interest. The antibody (or fragment) is preferably applied by overlaying the antibody (or fragment)

onto a biological sample. Through the use of such a procedure, it is possible to determine not only the presence of the protein of interest, but also its distribution, in a particular sample. A wide variety of well-known histological methods (such as staining procedures) can be utilized to achieve such in situ detection.

Immunoassays for a protein of interest typically comprise incubating a biological sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional methods.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which an antibody specific for a protein of interest can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.; Voller et al., 1978, *J. Clin. Pathol.* 31:507-520; Butler, J. E., 1981, *Meth. Enzymol.* 73:482-523; Maggio (ed.), 1980, *Enzyme Immunoassay*, CRC Press, Boca Raton, Fla.; Ishikawa et al., (eds.), 1981, *Enzyme Immunoassay*, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, 1986, *Principles of Radioimmunoassays*, Seventh Training Course on Radioligand Assay Techniques, The Endocrine Society, which is hereby incorporated by reference herein). The radioactive isotope (e.g., $^{125}$I, $^{131}$I, $^{35}$S or $^{3}$H) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In another embodiment, specific binding molecules other than antibodies, such as aptamers, may be used to bind the cellular constituents. In yet another embodiment, the cellular constituent profile may comprise a measurable aspect of an infectious agent (e.g., lipopolysaccharides or viral proteins) or a component thereof.

In some embodiments, a protein chip assay (e.g., The ProteinChip® Biomarker System, Ciphergen, Fremont, Calif.) is used to measure molecular profiles comprising discriminating proteins. See also, for example, Lin, 2004, *Modern Pathology*, 1-9; Li, 2004, *Journal of Urology* 171:1782-1787; Wadsworth, 2004, *Clinical Cancer Research* 10:1625-1632; Prieto, 2003, *Journal of Liquid Chromatography & Related Technologies* 26:2315-2328; Coombes, 2003, *Clinical Chemistry* 49:1615-1623; Mian, 2003, *Proteomics* 3:1725-1737; Lehre et al., 2003, *BJU International* 92:223-225; and Diamond, 2003, *Journal of the American Society for Mass Spectrometry* 14:760-765, each of which is hereby incorporated by reference in its entirety.

In some embodiments, a bead assay is used to measure molecular profiles comprising proteins. One such bead assay is the Becton Dickinson Cytometric Bead Array (CBA). CBA employs a series of particles with discrete fluorescence intensities to simultaneously detect multiple soluble analytes. CBA is combined with flow cytometry to create a multiplexed assay. The Becton Dickinson CBA system, as embodied for example in the Becton Dickinson Human Inflammation Kit, uses the sensitivity of amplified fluorescence detection by flow cytometry to measure soluble analytes in a particle-based immunoassay. Each bead in a CBA provides a capture surface for a specific protein and is analogous to an individually coated well in an ELISA plate. The BD CBA capture bead mixture is in suspension to allow for the detection of multiple analytes in a small volume sample.

In some embodiments the multiplex analysis method described in U.S. Pat. No. 5,981,180 ("the '180 patent"), herein incorporated by reference in its entirety, and in particular for its teachings of the general methodology, bead technology, system hardware and antibody detection, is used to measure molecular profiles. For this analysis, a matrix of microparticles is synthesized, where the matrix consists of different sets of microparticles. Each set of microparticles can have thousands of molecules of a distinct antibody capture reagent immobilized on the microparticle surface and can be color-coded by incorporation of varying amounts of two fluorescent dyes. The ratio of the two fluorescent dyes provides a distinct emission spectrum for each set of microparticles, allowing the identification of a microparticle a set following the pooling of the various sets of microparticles. U.S. Pat. Nos. 6,268,222 and 6,599,331 also are incorporated herein by reference in their entirety, and in particular for their teachings of various methods of labeling microparticles for multiplex analysis.

5.9.2. Other Types of Cellular Constituent Abundance Measurements

The methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plate, in which each well contains its own unique chemistry is provided. Each unique chemistry is designed to test a particular phenotype. Cells from the organism of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, *Genome Research* 11:1246-55.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry is provided. Each unique chemistry is designed to test a particular phenotype. Cells from a biological specimen obtained from the patient are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, *Genome Research* 11:1246-55.

In some embodiments of the present invention, the cellular constituents that are measured are metabolites. Metabolites include, but are not limited to, amino acids, metals, soluble sugars, sugar phosphates, and complex carbohydrates. Such metabolites can be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam), fourier-transform infrared spectrometry (Griffiths and de Haseth, 1986, *Fourier transform infrared spectrometry*, John Wiley, New York; Helm et al., 1991, *J. Gen. Microbiol.* 137:69-79; Naumann et al., 1991, *Nature* 351:81-82; Naumann et al., 1991, In: *Modern techniques for rapid microbiological analysis*, 43-96, Nelson, W. H., ed., VCH Publishers, New York), Raman spectrometry, gas chromatography-mass spectroscopy (GC-MS) (Fiehn et al., 2000, *Nature Biotechnology* 18:1157-1161, capillary electrophoresis (CE)/MS, high pressure liquid chromatography/mass spectroscopy (HPLC/MS), as well as liquid chromatography (LC)-Electrospray and cap-LC-tandem-electrospray mass spectrometries. Such methods can be combined with established chemometric methods that make use of artificial neural networks and genetic programming in order to discriminate between closely related samples.

In some embodiments, a separation method may be used to measure molecular profiles, such that only a subset of cellular constituents within the sample is analyzed. For example, the cellular constituents that are analyzed in a sample may be mRNA species from a cellular extract which has been fractionated to obtain only the nucleic acid cellular constituents within the sample, or the cellular constituents may be from a fraction of the total complement of proteins within the sample, which have been fractionated by chromatographic techniques.

Molecular profiles can also, for example, be measured by the use of one or more of the following methods described below. For example, methods may include nuclear magnetic resonance (NMR) spectroscopy, a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, Fourier transform mass spectrometry (FTMS) and ion trap. Other suitable methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

In one embodiment, laser desorption/ionization time-of-flight mass spectrometry is used to measure a molecular profiles where the cellular constituents are proteins or protein fragments that have been ionized and vaporized off an immobilizing support by incident laser radiation and the values measured for the molecular profiles are the presence or absence of peaks representing these fragments in the mass spectra profile. A variety of laser desorption/ionization techniques are known in the art (see, e.g., Guttman et al., 2001, *Anal. Chem.* 73:1252-62 and Wei et al., 1999, *Nature* 399: 243-246, each of which is hereby incorporated by herein be reference in its entirety).

Laser desorption/ionization time-of-flight mass spectrometry allows the generation of large amounts of information in a relatively short period of time. A biological sample is applied to one of several varieties of a support that binds all of the cellular constituents, or a subset thereof, in the sample. Cell lysates or samples are directly applied to these surfaces in volumes as small as 0.5 µL, with or without prior purification or fractionation. The lysates or sample can be concentrated or diluted prior to application onto the support surface. Laser desorption/ionization is then used to generate mass spectra of the sample, or samples, in as little as three hours.

5.10. Exemplary Diseases

Exemplary diseases for which clinical trials can be directed in accordance with the systems, methods, and apparatus of the present invention include, but are not limited to, asthma, cancers, common late-onset Alzheimer's disease, diabetes, heart disease, hereditary early-onset Alzheimer's disease (George-Hyslop et al., 1990, *Nature* 347:194), hereditary nonpolyposis colon cancer, hypertension, infection, maturity-onset diabetes of the young (Barbosa et al., 1976, *Diabete Metab.* 2:160), mellitus, nonalcoholic fatty liver (NAFL) (Younossi, et al., 2002, Hepatology 35:746-752), nonalcoholic steatohepatitis (NASH) (James & Day, 1998, *J. Hepatol.* 29:495-501), non-insulin-dependent diabetes mellitus, and polycystic kidney disease (Reeders et al., 1987, *Human Genetics* 76:348).

Cancers that studied in accordance with the present systems, methods, and apparatus include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

In some embodiments, cancers that studied in accordance with the present systems, methods, and apparatus include, but are not limited to, cancers, such as but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intraepithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

5.11. Exemplary Decision Rules

In one embodiment, comparison of a biomarker profile in a first plurality of biomarker profiles to biomarker profiles obtained from a training population is performed, and comprises applying a decision rule. The decision rule is constructed using a data analysis algorithm, such as a computer pattern recognition algorithm. Other suitable data analysis algorithms for constructing decision rules include, but are not limited to, logistic regression or a nonparametric algorithm that detects differences in the distribution of feature values (e.g., a Wilcoxon Signed Rank Test (unadjusted and adjusted)). The decision rule can be based upon measurement values for two, three, four, five, 10, 20 or more discriminating cellular constituents. Such measurements can be cellular constituent abundance values, absence or presence of genetic markers in the discriminating set of cellular constituents, or some other form of measurement. In one embodiment, the decision rule is based on hundreds of discriminating cellular constituents or more. Decision rules may also be built using a classification tree algorithm. For example, each biomarker profile from the training population can comprise at least three features, where the features are predictors in a classification tree algorithm. The decision rule predicts membership within a class (e.g., membership in the responder class or nonresponder class) with an accuracy of at least about at least about 70%, of at least about 75%, of at least about 80%, of at least about 85%, of at least about 90%, of at least about 95%, of at least about 97%, of at least about 98%, of at least about 99%, or about 100%.

Suitable data analysis algorithms are known in the art, some of which are reviewed in Hastie et al., supra. In a specific embodiment, a data analysis algorithm of the invention comprises Classification and Regression Tree (CART), Multiple Additive Regression Tree (MART), Prediction Analysis for Microarrays (PAM) or Random Forest analysis. Such algorithms classify complex spectra from biological materials, such as a blood sample, to distinguish subjects as normal or as possessing biomarker expression levels characteristic of a particular disease state. In other embodiments, a data analysis algorithm of the invention comprises ANOVA and nonparametric equivalents, linear discriminant analysis, logistic regression analysis, nearest neighbor classifier analysis, neural networks, principal component analysis, quadratic discriminant analysis, regression classifiers, and support vector machines. While such algorithms may be used to construct a decision rule and/or increase the speed and efficiency of the application of the decision rule and to avoid investigator bias, one of ordinary skill in the art will realize that computer-based algorithms are not required to carry out the methods of the present invention. Exemplary data analysis algorithms that can be used to identify molecular profiles in the first plurality of molecular profiles that match the molecular profiles in the responder set of biological samples are described in the following subsections.

5.11.1 Decision Trees

One type of decision rule that can be constructed using the training population is a decision tree. Here, the "data analysis algorithm" is any technique that can build the decision tree, whereas the final "decision tree" is the decision rule. A decision tree is constructed using a training population and specific data analysis algorithms. Decision trees are described generally by Duda, 2001, *Pattern Classification*, John Wiley & Sons, Inc., New York. pp. 395-396, which is hereby incorporated by reference herein. Tree-based methods partition the feature space into a set of rectangles, and then fit a model (like a constant) in each one.

The training population data includes the features (e.g., expression values, or some other observable) for the cellular constituents in the molecular profiles of the biological samples obtained from the training set population. One specific algorithm that can be used to construct a decision tree is a classification and regression tree (CART). Other specific decision tree algorithms include, but are not limited to, ID3, C4.5, MART, and Random Forests. CART, ID3, and C4.5 are described in Duda, 2001, *Pattern Classification*, John Wiley & Sons, Inc., New York. pp. 396-408 and pp. 411-412, which is hereby incorporated by reference herein. CART, MART, and C4.5 are described in Hastie et al., 2001, *The Elements of Statistical Learning*, Springer-Verlag, New York, Chapter 9, which is hereby incorporated by reference herein in its entirety. Random Forests are described in Breiman, 1999, "Random Forests—Random Features," Technical Report 567, Statistics Department, U.C.Berkeley, September 1999, which is hereby incorporated by reference herein in its entirety.

In some embodiments of the present invention, decision trees are used to classify subjects using a plurality of discriminating cellular constituents. Decision tree algorithms belong to the class of supervised learning algorithms. The aim of a decision tree is to induce a classifier (a tree) from real-world example data. This tree can be used to classify unseen examples that have not been used to derive the decision tree. As such, a decision tree is derived from training data. Exemplary training data contains data for a plurality of subjects (the training population). For each respective subject there is a plurality of features in the class of the respective subject (e.g., responder/nonresponder). In one embodiment of the present invention, the training data is expression data for a combination of cellular constituents across the training population.

The following algorithm describes an exemplary decision tree derivation:

Tree (Examples,Class,Features)

Create a root node

If all Examples have the same Class value, give the root this label

Else if Features is empty label the root according to the most common value

Else begin

Calculate the information gain for each Feature

Select the Feature A with highest information gain and make this the root Feature For each possible value, v, of this Feature Add a new branch below the root, corresponding to A=v Let Examples (v) be those examples with A=v If Examples (v) is empty, make the new branch a leaf node labeled with the most common value among Examples Else let the new branch be the tree created by Tree (Examples (v),Class,Features−{A})

end

A more detailed description of the calculation of information gain is shown in the following. If the possible classes $v_i$ of the examples have probabilities $P(v_i)$ then the information content I of the actual answer is given by:

$$I(P(v_1), \ldots, P(v_n)) = \sum_{i=1}^{n} -P(v_i)\log_2 P(v_i)$$

The I-value shows how much information is needed in order to be able to describe the outcome of a classification for the specific dataset used. Supposing that the dataset contains p positive (e.g. is a responder) and n negative (e.g. is not a responder) examples (e.g. subjects), the information contained in a correct answer is:

$$I\left(\frac{p}{p+n}, \frac{n}{p+n}\right) = -\frac{p}{p+n}\log_2\frac{p}{p+n} - \frac{n}{p+n}\log_2\frac{n}{p+n}$$

where $\log_2$ is the logarithm using base two. By testing single features the amount of information needed to make a correct classification can be reduced. The remainder for a specific feature A (e.g. representing a specific biomarker) shows how much the information that is needed can be reduced.

$$\text{Remainder}(A) = \sum_{i=1}^{v} \frac{p_i + n_i}{p+n} I\left(\frac{p_i}{p_i+n_i}, \frac{n_i}{p_i+n_i}\right)$$

"v" is the number of unique attribute values for feature A in a certain dataset, "i" is a certain attribute value, "$p_i$" is the number of examples for feature A where the classification is positive (e.g. is a responder), "$n_i$" is the number of examples for feature A where the classification is negative (e.g. is not a responder).

The information gain of a specific feature A is calculated as the difference between the information content for the classes and the remainder of feature A:

$$\text{Gain}(A) = I\left(\frac{p}{p+n}, \frac{n}{p+n}\right) - \text{Remainder}(A)$$

The information gain is used to evaluate how important the different features are for the classification (how well they split up the examples), and the feature with the highest information.

In general there are a number of different decision tree algorithms, many of which are described in Duda, Pattern Classification, Second Edition, 2001, John Wiley & Sons, Inc. Decision tree algorithms often require consideration of feature processing, impurity measure, stopping criterion, and pruning. Specific decision tree algorithms include, but are not limited to classification and regression trees (CART), multivariate decision trees, ID3, and C4.5.

In one approach, when a decision tree is used, the cellular constituent abundance data for a select combination of cellular constituents (discriminating cellular constituents) across a training population is standardized to have mean zero and unit variance. The members of the training population are randomly divided into a training set and a test set. For example, in one embodiment, two thirds of the members of the training population are placed in the training set and one third of the members of the training population are placed in the test set. The expression values for a select combination of biomarkers described in the present invention is used to construct the decision tree. Then, the ability for the decision tree to correctly classify members in the test set is determined. In some embodiments, this computation is performed several times for a given combination of biomarkers. In each computational iteration, the members of the training population are randomly assigned to the training set and the test set. Then, the quality of the combination of cellular constituents is taken as the average of each such iteration of the decision tree computation.

In addition to univariate decision trees in which each split is based on a measured value for a corresponding cellular constituent, among the set of discriminating cellular constituents, or the relative feature values of two such cellular constituents, multivariate decision trees can be implemented as a decision rule. In such multivariate decision trees, some or all of the decisions actually comprise a linear combination of feature values for a plurality of cellular constituents of the present invention. Such a linear combination can be trained using known techniques such as gradient descent on a classification or by the use of a sum-squared-error criterion. To illustrate such a decision tree, consider the expression:

$$0.04x_1 + 0.16x_2 < 500$$

Here, $x_1$ and $x_2$ refer to two different features for two different cellular constituents from among the discriminating cellular constituents. To poll the decision rule, the values of features $x_1$ and $x_2$ are obtained from the measurements obtained from the unclassified subject. These values are then inserted into the equation. If a value of less than 500 is computed, then a first branch in the decision tree is taken. Otherwise, a second branch in the decision tree is taken. Multivariate decision trees are described in Duda, 2001, Pattern Classification, John Wiley & Sons, Inc., New York, pp. 408-409, which is hereby incorporated by reference.

Another approach that can be used in the present invention is multivariate adaptive regression splines (MARS). MARS is an adaptive procedure for regression, and is well suited for the high-dimensional problems addressed by the present invention. MARS can be viewed as a generalization of stepwise linear regression or a modification of the CART method to improve the performance of CART in the regression setting. MARS is described in Hastie et al., 2001, The Elements of Statistical Learning, Springer-Verlag, New York, pp. 283-295, which is hereby incorporated by reference in its entirety.

5.11.2 Predictive Analysis of Microarrays (PAM)

One approach to developing a decision rule using discriminating cellular constituents is the nearest centroid classifier. Such a technique computes, for each class (responders versus nonresponders), a centroid given by the average feature levels of the cellular constituents in the class, and then assigns new samples to the class whose centroid is nearest. This approach is similar to k-means clustering except clusters are replaced by known classes. This algorithm can be sensitive to noise when a large number of cellular constituents are used. One enhancement to the technique uses shrinkage: for each cellular constituent, differences between class centroids are set to zero if they are deemed likely to be due to chance. This approach is implemented in the Prediction Analysis of Microarray, or PAM. See, for example, Tibshirani et al., 2002, Proc. Natl. Acad. Sci. USA 99:6567-6572, which is hereby incorporated by reference in its entirety. Shrinkage is controlled by a threshold below which differences are considered noise. Cellular constituents that show no difference above the noise level are removed. A threshold can be chosen by cross-validation. As the threshold is decreased, more cellular constituents are included and estimated classification errors decrease, until they reach a bottom and start climbing again as a result of noise cellular constituents—a phenomenon known as overfitting.

5.11.3 Bagging, Boosting, and the Random Subspace Method

Bagging, boosting, the random subspace method, and additive trees are data analysis algorithms known as combining techniques that can be used to improve weak decision rules. These techniques are designed for, and usually applied to, decision trees, such as the decision trees described above. In addition, such techniques can also be useful in decision rules developed using other types of data analysis algorithms such as linear discriminant analysis.

In bagging, one samples the training set, generating random independent bootstrap replicates, constructs the decision rule on each of these, and aggregates them by a simple majority vote in the final decision rule. See, for example, Breiman, 1996, Machine Learning 24, 123-140; and Efron & Tibshirani, An Introduction to Boostrap, Chapman & Hall, New York, 1993, which is hereby incorporated by reference in its entirety.

In boosting, decision rules are constructed on weighted versions of the training set, which are dependent on previous classification results. Initially, all cellular constituents under consideration have equal weights, and the first decision rule is constructed on this data set. Then, weights are changed according to the performance of the decision rule. Erroneously classified features get larger weights, and the next decision rule is boosted on the reweighted training set. In this way, a sequence of training sets and decision rules is obtained, which is then combined by simple majority voting or by weighted majority voting in the final decision rule. See, for example, Freund & Schapire, "Experiments with a new boosting algorithm," Proceedings 13th International Conference on Machine Learning, 1996, 148-156, which is hereby incorporated by reference in its entirety.

To illustrate boosting, consider the case where there are two phenotypes exhibited by the population under study, phenotype 1 (e.g., responder), and phenotype 2 (e.g., SIRS only, meaning that the subject is not a responder). Given a vector of predictor cellular constituents (e.g., a vector of features that represent such cellular constituents) from the training set data, a decision rule G(X) produces a prediction taking one of the type values in the two value set:{phenotype 1, phenotype 2}. The error rate on the training sample is $$\overline{err} = \frac{1}{N} \sum_{i=1}^{N} I(y_i \neq G(x_i))$$

where N is the number of subjects in the training set (the sum total of the subjects that have either phenotype 1 or phenotype 2). For example, if there are 49 organisms that are responders and 72 organisms that are not responders, N is 121. A weak decision rule is one whose error rate is only slightly better than random guessing. In the boosting algorithm, the weak decision rule is repeatedly applied to modified versions of the data, thereby producing a sequence of weak decision rules $G_m(x)$, m, =1, 2, . . . , M. The predictions from all of the decision rules in this sequence are then combined through a weighted majority vote to produce the final decision rule:

$$G(x) = \text{sign}\left(\sum_{m=1}^{M} \alpha_m G_m(x)\right)$$

Here $\alpha_1, \alpha_2, \ldots, \alpha_M$ are computed by the boosting algorithm and their purpose is to weigh the contribution of each respective decision rule Gm(x). Their effect is to give higher influence to the more accurate decision rules in the sequence.

The data modifications at each boosting step consist of applying weights $w_1, w_2, \ldots, w_n$ to each of the training observations $(x_i, y_i)$, i=1, 2, . . . , N. Initially all the weights are set to $w_i=1/N$, so that the first step simply trains the decision rule on the data in the usual manner. For each successive iteration m=2, 3, . . . , M the observation weights are individually modified and the decision rule is reapplied to the weighted observations. At step m, those observations that were misclassified by the decision rule $G_m-1(x)$ induced at the previous step have their weights increased, whereas the weights are decreased for those that were classified correctly. Thus as iterations proceed, observations that are difficult to correctly classify receive ever-increasing influence. Each successive decision rule is thereby forced to concentrate on those training observations that are missed by previous ones in the sequence.

The exemplary boosting algorithm is summarized as follows:

1. Initialize the observation weights $w_i = 1/N$, i = 1, 2, ..., N.
2. For m = 1 to M:
    (a) Fit a decision rule $G_m(x)$ to the training set using weights $w_i$.
    (b) Compute $$err_m = \frac{\sum_{i=1}^{N} w_i I(y_i \neq G_m(x_i))}{\sum_{i=1}^{N} w_i}$$

(c) Compute $\alpha_m = \log((1-eff_m)/err_m)$.

(d) Set $w_i \leftarrow w_i \cdot \exp[\alpha_m \cdot I(y_i \neq G_m(x_i))]$, i = 1, 2, ..., N.

3. Output $G(x) = \text{sign}\left[\sum_{m=1}^{M} \alpha_m G_m(x)\right]$

In one embodiment in accordance with this algorithm, each object is, in fact, a factor. Furthermore, in the algorithm, the current decision rule $G_m(x)$ is induced on the weighted observations at line 2a. The resulting weighted error rate is computed at line 2b. Line 2c calculates the weight $\alpha_m$ given to $G_m(x)$ in producing the final classifier G(x) (line 3). The individual weights of each of the observations are updated for the next iteration at line 2d. Observations misclassified by $G_m(x)$ have their weights scaled by a factor $\exp(\alpha_m)$, increasing their relative influence for inducing the next classifier $G_m+1(x)$ in the sequence. In some embodiments, modifications of the Freund and Schapire, 1997, Journal of Computer and System Sciences 55, pp. 119-139, boosting methods are used. See, for example, Hasti et al., *The Elements of Statistical Learning*, 2001, Springer, N.Y., Chapter 10, which is hereby incorporated by reference in its entirety. For example, in some embodiments, feature preselection is performed using a technique such as the nonparametric scoring methods of Park et al., 2002, *Pac. Symp. Biocomput.* 6:52-63, which is hereby incorporated by reference in its entirety. Feature preselection is a form of dimensionality reduction in which the genes that discriminate between classifications the best are selected for use in the classifier. Then, the LogitBoost procedure introduced by Friedman et al., 2000, *Ann. Stat.* 28:337-407 is used rather than the boosting procedure of Freund and Schapire. In some embodiments, the boosting and other classification methods of Ben-Dor et al., 2000, *Journal of Computational Biology* 7:559-583, hereby incorporated by reference in its entirety, are used in the present invention. In some embodiments, the boosting and other classification methods of Freund and Schapire, 1997, *Journal of Computer and System Sciences* 55:119-139, hereby incorporated by reference in its entirety, are used.

In the random subspace method, decision rules are constructed in random subspaces of the data feature space. These decision rules are usually combined by simple majority voting in the final decision rule. See, for example, Ho, "The Random subspace method for constructing decision forests," *IEEE Trans Pattern Analysis and Machine Intelligence*, 1998; 20(8): 832-844, which is hereby incorporated by reference in its entirety.

5.5.4 Multiple Additive Regression Trees

Multiple additive regression trees (MART) represents another way to construct a decision rule that can be used in the present invention. A generic algorithm for MART is:

1. Initialize $f0(x) = \text{argmin}_\gamma \sum_{i=1}^{N} L(y_i, \gamma)$.
2. For m = 1 to M:
    (a) For I = 1,2, ..., N compute $$r_{im} = -\left[\frac{\partial L(y_i, f(x_i))}{\partial f(x_i)}\right]_{f=f_{m-i}}$$

(b) Fit a regression tree to the targets rim giving terminal regions Rjm, j = 1,2, ..., Jm.
    (c) For j = 1, 2, ..., Jm compute -continued $$\gamma_{jm} = \underset{\gamma}{\mathrm{argmin}} \sum_{x_i \in R_{jm}} L(y_i, f_{m-1}(x_i) + \gamma)$$

(d) Update $fm(x) = fm - 1(x) + \sum_{j=1}^{J_m} \gamma_{jm} I(x \in R_{jm})$

3. Ouput $\hat{f}(x) = f_M(x)$.

Specific algorithms are obtained by inserting different loss criteria $L(y, f(x))$. The first line of the algorithm initializes to the optimal constant model, which is just a single terminal node tree. The components of the negative gradient computed in line 2(a) are referred to as generalized pseudo residuals, r. Gradients for commonly used loss functions are summarized in Table 10.2, of Hastie et al., 2001, *The Elements of Statistical Learning*, Springer-Verlag, New York, p. 321, which is hereby incorporated by reference. The algorithm for classification is similar and is described in Hastie et al., Chapter 10, which is hereby incorporated by reference in its entirety. Tuning parameters associated with the MART procedure are the number of iterations M and the sizes of each of the constituent trees $J_m$, m=1, 2, . . . , M.

5.11.5 Decision Rules Derived by Regression

In some embodiments, a decision rule used to classify subjects is built using regression. In such embodiments, the decision rule can be characterized as a regression classifier, preferably a logistic regression classifier. Such a regression classifier includes a coefficient for each of the cellular constituents (e.g., a feature for each such cellular constituent) used to construct the classifier. In such embodiments, the coefficients for the regression classifier are computed using, for example, a maximum likelihood approach. In such a computation, the features for the cellular constituents (e.g., RT-PCR, microarray data) is used. In particular embodiments, molecular marker data from only two trait subgroups is used (e.g., trait subgroup a are responders and trait subgroup b are not responders) and the dependent variable is absence or presence of a particular trait in the subjects for which cellular constituent data is available.

In another specific embodiment, the training population comprises a plurality of trait subgroups (e.g., three or more trait subgroups, four or more specific trait subgroups, etc.). These multiple trait subgroups can correspond to discrete levels of response to therapy. In this specific embodiment, a generalization of the logistic regression model that handles multicategory responses can be used to develop a decision that discriminates between the various trait subgroups found in the training population. For example, measured data for selected molecular markers can be applied to any of the multi-category logit models described in Agresti, *An Introduction to Categorical Data Analysis*, 1996, John Wiley & Sons, Inc., New York, Chapter 8, hereby incorporated by reference in its entirety, in order to develop a classifier capable of discriminating between any of a plurality of trait subgroups represented in a training population.

5.11.6 Neural Networks

In some embodiments, the feature data measured for select cellular constituents of the present invention (e.g., RT-PCR data, mass spectrometry data, microarray data) can be used to train a neural network. A neural network is a two-stage regression or classification decision rule. A neural network has a layered structure that includes a layer of input units (and the bias) connected by a layer of weights to a layer of output units. For regression, the layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference in its entirety. Neural networks are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, N.Y., each of which is hereby incorporated by reference in its entirety. What is disclosed below is some exemplary forms of neural networks.

The basic approach to the use of neural networks is to start with an untrained network, present a training pattern to the input layer, and to pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. For regression, this error can be sum-of-squared errors. For classification, this error can be either squared error or cross-entropy (deviation). See, e.g., Hastie et al., 2001, *The Elements of Statistical Learning*, Springer-Verlag, New York, which is hereby incorporated by reference in its entirety.

Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the classifier defined by the network topology. In batch training, all patterns are presented to the network before learning takes place. Typically, in batch training, several passes are made through the training data. In online training, each pattern is presented once and only once to the net.

In some embodiments, consideration is given to starting values for weights. If the weights are near zero, then the operative part of the sigmoid commonly used in the hidden layer of a neural network (see, e.g., Hastie et al., 2001, *The Elements of Statistical Learning*, Springer-Verlag, New York, hereby incorporated by reference) is roughly linear, and hence the neural network collapses into an approximately linear classifier. In some embodiments, starting values for weights are chosen to be random values near zero. Hence the classifier starts out nearly linear, and becomes nonlinear as the weights increase. Individual units localize to directions and introduce nonlinearities where needed. Use of exact zero weights leads to zero derivatives and perfect symmetry, and the algorithm never moves. Alternatively, starting with large weights often leads to poor solutions.

Since the scaling of inputs determines the effective scaling of weights in the bottom layer, it can have a large effect on the quality of the final solution. Thus, in some embodiments, at the outset all expression values are standardized to have mean zero and a standard deviation of one. This ensures all inputs are treated equally in the regularization process, and allows one to choose a meaningful range for the random starting weights. With standardization inputs, it is typical to take random uniform weights over the range [−0.7, +0.7].

A recurrent problem in the use of three-layer networks is the optimal number of hidden units to use in the network. The number of inputs and outputs of a three-layer network are determined by the problem to be solved. In the present invention, the number of inputs for a given neural network will equal the number of cellular constituents selected from the training population. The number of output for the neural network will typically be just one. However, in some embodiments more than one output is used so that more than just two states can be defined by the network. For example, a multi-output neural network can be used to discriminate between responders and nonresponders. If too many hidden units are used in a neural network, the network will have too many degrees of freedom and is trained too long, there is a danger that the network will overfit the data. If there are too few hidden units, the training set cannot be learned. Generally speaking, however, it is better to have too many hidden units than too few. With too few hidden units, the classifier might not have enough flexibility to capture the nonlinearities in the date; with too many hidden units, the extra weight can be shrunk towards zero if appropriate regularization or pruning, as described below, is used. In typical embodiments, the number of hidden units is somewhere in the range of 5 to 100, with the number increasing with the number of inputs and number of training cases.

One general approach to determining the number of hidden units to use is to apply a regularization approach. In the regularization approach, a new criterion function is constructed that depends not only on the classical training error, but also on classifier complexity. Specifically, the new criterion function penalizes highly complex classifiers; searching for the minimum in this criterion is to balance error on the training set with error on the training set plus a regularization term, which expresses constraints or desirable properties of solutions:

$$J = J_{pat} + \lambda J_{reg}.$$

The parameter $\lambda$ is adjusted to impose the regularization more or less strongly. In other words, larger values for $\lambda$ will tend to shrink weights towards zero: typically cross-validation with a validation set is used to estimate $\lambda$. This validation set can be obtained by setting aside a random subset of the training population. Other forms of penalty have been proposed, for example the weight elimination penalty (see, e.g., Hastie et al., 2001, *The Elements of Statistical Learning*, Springer-Verlag, New York, hereby incorporated by reference).

Another approach to determine the number of hidden units to use is to eliminate—prune—weights that are least needed. In one approach, the weights with the smallest magnitude are eliminated (set to zero). Such magnitude-based pruning can work, but is nonoptimal; sometimes weights with small magnitudes are important for learning and training data. In some embodiments, rather than using a magnitude-based pruning approach, Wald statistics are computed. The fundamental idea in Wald Statistics is that they can be used to estimate the importance of a hidden unit (weight) in a classifier. Then, hidden units having the least importance are eliminated (by setting their input and output weights to zero). Two algorithms in this regard are the Optimal Brain Damage (OBD) and the Optimal Brain Surgeon (OBS) algorithms that use second-order approximation to predict how the training error depends upon a weight, and eliminate the weight that leads to the smallest increase in training error.

Optimal Brain Damage and Optimal Brain Surgeon share the same basic approach of training a network to local minimum error at weight w, and then pruning a weight that leads to the smallest increase in the training error. The predicted functional increase in the error for a change in full weight vector $\delta w$ is:

$$\delta J = \left(\frac{\partial J}{\partial w}\right)' \cdot \delta w + \frac{1}{2} \delta w' \cdot \frac{\partial^2 J}{\partial w^2} \cdot \delta w + O(\|\delta w\|^3)$$

where $$\frac{\partial^2 J}{\partial w^2}$$

is the Hessian matrix. The first term vanishes at a local minimum in error; third and higher order terms are ignored. The general solution for minimizing this function given the constraint of deleting one weight is:

$$\delta w = -\frac{w_q}{[H^{-1}]_{qq}} H^{-1} \cdot u_q \text{ and } L_q = \frac{1}{2} \cdot \frac{w_q^2}{[H^{-1}]_{qq}}$$

Here, $u_q$ is the unit vector along the qth direction in weight space and $L_q$ is approximation to the saliency of the weight q—the increase in training error if weight q is pruned and the other weights updated $\delta w$. These equations require the inverse of H. One method to calculate this inverse matrix is to start with a small value, $H_0^{-1} = \alpha^{-1} I$, where $\alpha$ is a small parameter—effectively a weight constant. Next the matrix is updated with each pattern according to $$H_{m+1}^{-1} = H_m^{-1} - \frac{H_m^{-1} X_{m+1} X_{m+1}^T H_m^{-1}}{\frac{n}{a_m} + X_{m+1}^T H_m^{-1} X_{m+1}} \qquad \text{Eqn. 1}$$

where the subscripts correspond to the pattern being presented and $a_m$ decreases with m. After the full training set has been presented, the inverse Hessian matrix is given by $H^{-1} = H_n^{-1}$. In algorithmic form, the Optimal Brain Surgeon method is:

```
begin initialize n_H, w, θ
    train a reasonably large network to minimum error
        do compute H⁻¹ by Eqn. 1
            q* ← arg min w_q² / (2[H⁻¹]_qq)(saliency L_q)
                     q
            w ← w − (w_q* / [H⁻¹]_q*q*) H⁻¹ e_q*  (saliency L_q)
        until J(w) > θ
    return w
end
```

The Optimal Brain Damage method is computationally simpler because the calculation of the inverse Hessian matrix in line 3 is particularly simple for a diagonal matrix. The above algorithm terminates when the error is greater than a criterion initialized to be $\theta$. Another approach is to change line 6 to terminate when the change in J(w) due to elimination of a weight is greater than some criterion value. In some embodiments, the back-propagation neural network See, for example Abdi, 1994, "A neural network primer," *J. Biol System.* 2:247-283, hereby incorporated by reference in its entirety.

5.11.7 Clustering

In some embodiments, discriminating cellular constituents are used to cluster a training set. For example, consider the case in which ten features (corresponding to ten cellular constituents) described in the present invention are used. Each member m of the training population will have feature values (e.g. expression values) for each of the ten cellular constituents. Such values from a member m in the training population define a vector X where the components of the vector, $X_{im}$, are the expression level of the $i^{th}$ cellular constituent in organism m. If there are m organisms in the training set, selection of i cellular constituents will define m vectors. Note that the methods of the present invention do not require that each the expression value of every single cellular constituent used in the vectors be represented in every single vector m. In other words, data from a subject in which one of the $i^{th}$ cellular constituents is not found can still be used for clustering. In such instances, the missing expression value is assigned either a "zero" or some other normalized value. In some embodiments, prior to clustering, the feature values are normalized to have a mean value of zero and unit variance.

Those members of the training population that exhibit similar expression patterns across the training group will tend to cluster together. A particular combination of genes of the present invention is considered to be a good classifier in this aspect of the invention when the vectors cluster into the trait groups found in the training population. For instance, if the training population includes class a: subjects that are responders, and class b: subjects that are not responders, an ideal clustering classifier will cluster the population into two groups, with one cluster group uniquely representing class a and the other cluster group uniquely representing class b.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973.

More recently, Duda et al., Pattern Classification, $2^{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

5.11.8 Principal Component Analysis

Principal component analysis (PCA) has been proposed to analyze gene expression data. More generally, PCA can be used to analyze discriminating cellular constituents of the present invention in order to construct a decision rule that discriminates responders from nonresponders. Principal component analysis is a classical technique to reduce the dimensionality of a data set by transforming the data to a new set of variable (principal components) that summarize the features of the data. See, for example, Jolliffe, 1986, *Principal Component Analysis*, Springer, N.Y., which is hereby incorporated by reference. Principal component analysis is also described in Draghici, 2003, *Data Analysis Tools for DNA Microarrays*, Chapman & Hall/CRC, which is hereby incorporated by reference. What follows is non-limiting examples of principal components analysis.

Principal components (PCs) are uncorrelated and are ordered such that the $k^{th}$ PC has the kth largest variance among PCs. The $k^{th}$ PC can be interpreted as the direction that maximizes the variation of the projections of the data points such that it is orthogonal to the first k−1 PCs. The first few PCs capture most of the variation in the data set. In contrast, the last few PCs are often assumed to capture only the residual 'noise' in the data.

PCA can also be used to create a classifier in accordance with the present invention. In such an approach, vectors for the discriminating cellular constituents can be constructed in the same manner described for clustering above. In fact, the set of vectors, where each vector represents the feature values (e.g., abundance values) for the discriminating cellular constituents from a particular member of the training population, can be viewed as a matrix. In some embodiments, this matrix is represented in a Free-Wilson method of qualitative binary description of monomers (Kubinyi, 1990, *3D QSAR in drug design theory methods and applications*, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been considered.

Then, each of the vectors (where each vector represents a member of the training population) is plotted. Many different types of plots are possible. In some embodiments, a one-dimensional plot is made. In this one-dimensional plot, the value for the first principal component from each of the members of the training population is plotted. In this form of plot, the expectation is that members of a first subgroup (e.g. those subjects that are responders) will cluster in one range of first principal component values and members of a second subgroup (e.g., those subjects that are not responders) will cluster in a second range of first principal component values.

In one ideal example, the training population comprises two subgroups: "responders" and "nonresponders." The first principal component is computed using the molecular marker expression values for the select cellular constituents of the present invention across the entire training population data set. Then, each member of the training set is plotted as a function of the value for the first principal component. In this ideal example, those members of the training population in which the first principal component is positive are the "responders" and those members of the training population in which the first principal component is negative are "subjects that are not responders."

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent subjects that are responders and a second cluster of members in the two-dimensional plot will represent subjects that are not responders.

5.11.9 Nearest Neighbor Analysis

Nearest neighbor classifiers are memory-based and require no classifier to be fit. Given a query point $x_0$, the k training points $x_{(r)}$, r, ..., k closest in distance to $x_0$ are identified and then the point $x_0$ is classified using the k nearest neighbors. Ties can be broken at random. In some embodiments, Euclidean distance in feature space is used to determine distance as:

$$d_{(i)} = \|x_{(i)} - x_0\|.$$

Typically, when the nearest neighbor algorithm is used, the expression data used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. A select combination of cellular constituents of the present invention represents the feature space into which members of the test set are plotted. Next, the ability of the training set to correctly characterize the members of the test set is computed. In some embodiments, nearest neighbor computation is performed several times for a given combination of cellular constituents of the present invention. In each iteration of the computation, the members of the training population are randomly assigned to the training set and the test set. Then, the quality of the combination of cellular constituents is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, *The Elements of Statistical Learning*, Springer, N.Y., each of which is hereby incorporated by reference in its entirety.

5.11.10 Linear Discriminant Analysis

Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, select combinations of discriminating cellular constituents across a subset of the training population serve as the requisite continuous independent variables. The trait subgroup classification of each of the members of the training population serves as the dichotomous categorical dependent variable.

LDA seeks the linear combination of variables that maximizes the ratio of between-group variance and within-group variance by using the grouping information. Implicitly, the linear weights used by LDA depend on how the feature values of a molecular marker across the training set separates in the two groups (e.g., a group a that are responders and a group b that are not responders) and how these feature values correlate with the feature values of other cellular constituents. In some embodiments, LDA is applied to the data matrix of the N members in the training sample by K cellular constituents in a combination of cellular constituents described in the present invention. Then, the linear discriminant of each member of the training population is plotted. Ideally, those members of the training population representing a first subgroup (e.g. those subjects that are responders) will cluster into one range of linear discriminant values (e.g., negative) and those member of the training population representing a second subgroup (e.g. those subjects that are not responders) will cluster into a second range of linear discriminant values (e.g., positive). The LDA is considered more successful when the separation between the clusters of discriminant values is larger. For more information on linear discriminant analysis, see Duda, *Pattern Classification*, Second Edition, 2001, John Wiley & Sons, Inc; and Hastie, 2001, *The Elements of Statistical Learning*, Springer, N.Y.; and Venables & Ripley, 1997, *Modern Applied Statistics with s-plus*, Springer, N.Y., each of which is hereby incorporated by reference in its entirety.

5.11.11 Quadratic Discriminant Analysis

Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

5.11.12 Support Vector Machines

In some embodiments of the present invention, support vector machines (SVMs) are used to classify subjects using measurement values for discriminating cellular constituents from the training population. SVMs are a relatively new type of learning algorithm. See, for example, Cristianini and Shawe-Taylor, 2000, An Introduction to Support Vector Machines, Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y., Duda, Pattern Classification, Second Edition, 2001, John Wiley & Sons, Inc.; and Hastie, 2001, The Elements of Statistical Learning, Springer, N.Y.; and Furey et al., 2000, *Bioinformatics* 16:906-914, each of which is hereby incorporated by reference in its entirety. When used for classification, SVMs separate a given set of binary labeled data training data with a hyper-plane that is maximally distance from them. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

In one approach, when a SVM is used, the measurement data for the discriminating cellular constituents is standardized to have mean zero and unit variance and the members of a training population are randomly divided into a training set and a test set. For example, in one embodiment, two thirds of the members of the training population are placed in the training set and one third of the members of the training population are placed in the test set. The abundance values for a combination of discriminating cellular constituents across the training population is used to train the SVM. Then the ability for the trained SVM to correctly classify members in the test set is determined. In some embodiments, this computation is performed several times for a given combination of cellular constituents. In each iteration of the computation, the members of the training population are randomly assigned to the training set and the test set. Then, the quality of the combination of cellular constituents is taken as the average of each such iteration of the SVM computation.

5.11.13 Evolutionary Methods

Inspired by the process of biological evolution, evolutionary methods of decision rule design employ a stochastic search for an decision rule. In broad overview, such methods create several decision rules—a population—from a combination of cellular constituents described in the present invention. Each decision rule varies somewhat from the other. Next, the decision rules are scored on feature data across the training population. In keeping with the analogy with biological evolution, the resulting (scalar) score is sometimes called the fitness. The decision rules are ranked according to their score and the best decision rules are retained (some portion of the total population of decision rules). Again, in keeping with biological terminology, this is called survival of the fittest. The decision rules are stochastically altered in the next generation—the children or offspring. Some offspring decision rules will have higher scores than their parent in the previous generation, some will have lower scores. The overall process is then repeated for the subsequent generation: the decision rules are scored and the best ones are retained, randomly altered to give yet another generation, and so on. In part, because of the ranking, each generation has, on average, a slightly higher score than the previous one. The process is halted when the single best decision rule in a generation has a score that exceeds a desired criterion value. More information on evolutionary methods is found in, for example, Duda, *Pattern Classification*, Second Edition, 2001, John Wiley & Sons, Inc.

5.11.14 Other Data Analysis Algorithms

The data analysis algorithms described above are merely examples of the types of methods that can be used to construct a decision rule for discriminating converters from nonconverters. Moreover, combinations of the techniques described above can be used. Some combinations, such as the use of the combination of decision trees and boosting, have been described. However, many other combinations are possible. In addition, in other techniques in the art such as Projection Pursuit and Weighted Voting can be used to construct decision rules.

6. EXAMPLE

The following examples are provided in order to illustrate the many advantages of the present invention.

6.1. Classifying Tumor Types

The present example utilizes known databases composed of informative genes whose expression correlates with a class distinction between samples, for example a cancer class distinction. Databases that can be used in the present example include those described in U.S. Pat. No. 6,647,341; Golub et al., 1999, "Molecular Classification of Cancer: Class Discovery and Class Prediction by Gene Expression Monitoring," *Science* 286:531-537; Bhattacharjee et al., 2001, "Classification of human lung carcinomas by mRNA expression profiling reveals distinct adenocarcinoma subclasses," *Proc. Natl. Acad. Sci. USA* 98(24):13790-13795; Ramaswamy et al., 2003, "A molecular signature of metastasis in primary solid tumors," *Nature Genetics* 33:1-6; Su et al., 2001, "Molecular Classification of Human Gene Expression Signatures," *Cancer Research* 61:7388-7398; and Khan et al., 2001, "Classification and diagnostic prediction of cancers using gene expression profiling and artificial neural networks," *Nature Medicine* 7(6):673-679, each of which is hereby incorporated by reference in its entirety.

In one embodiment, the example uses hybridization patterns generated on available high-density gene discovery microarrays to profile diverse tumor types and develop a molecular expression phenotype that is used to classify tumor types. The example classifies unknown tumor types based on the correlation of the unknown tumor's genetic expression compared to the genetic expression of known tumor types by first performing a nonparametric statistical analysis on the known data, training an artificial neural network with the known data, and then inputting the unknown tumor data into the neural network.

In general, the example also provides a method for classifying objects based on characteristics comprising performing the steps of: a) receiving observation data corresponding to characteristics of known classes of objects (e.g. cellular constituent abundance data for cellular constituents whose abundance values discriminate between the known classes of objects); b) identifying classes most highly correlated with the characteristics of the known classes of objects; c) selecting, from among the identified characteristics, a set of characteristics that distinguish among the known classes of objects (e.g., a discriminating set of cellular constituents); d) providing the class characteristics as input to train a pattern classification algorithm (classifier) such as a neural network-based classifier; e) training the classifier to identify unknown objects based on class characteristics of the known objects; f) receiving sample data corresponding to characteristics of an unknown object; g) providing the sample data to the trained classifier (e.g., trained neural network); and h) calculating the likelihood that the unknown object is a member of each known class of objects based on the correlation between the class characteristics (e.g. cellular constituent abundance values for discriminating cellular constituents) of each of the known objects and the characteristics of the unknown object.

As a first step in the analysis of microarray data, genes that best represent a therapeutically effective response in a specific disease state with respect to a given therapy of interest (e.g. one or more chemical agents, one or more pharmaceutical drugs, etc.) are identified. In some embodiments, such genes are discriminating genes whose values discriminate between responders and nonresponders. Measurement values for such genes (e.g., abundance values of mRNA or cDNA copies of such genes) in biological samples may be measured before therapy and compared). Alternative, differential measurement values for such genes (e.g., abundance values of mRNA or cDNA copies of such genes) in biological samples may be measured before and after therapy may be made and compared. Regardless of measurement protocol, such measurements are referred to as profiles in this example. Such profiles can then be compared against gene profiles for other disease states to predict the efficacy of the given therapy of interest in treating other disease states. Such comparison analysis can be performed using significance analysis of microarrays (SAM) or any other microar7ray analysis (e.g., clustering methods such as those disclosed by Eisen et al., 1998, *Proc. Natl Acad. Sci. USA* 95:14863-14868; Alon et al., 1999, *Proc. Natl Acad. Sci. USA* 96:6745-6750; and Ben-Dor et al., 2000, *J. Comput. Biol.* 7:559-583; classification trees such as those disclosed by Dubitzky et al., 2001, *IEEE Eng. Med. Biol. Mag.* 20(4):75-83; genetic algorithms such as those disclosed by Li et al., 2001 in Methods of Microarray Data Analysis, Kluwer Academic Publishers; neural networks such as those disclosed by Hwang et al., 2001, in Methods of Microarray Data Analysis, Kluwer Academic Publishers; and the "Neighborhood Analysis" (a weighted correlation method) as disclosed by Golub et al., 1999, *Science* 286:531-537, each of which is hereby incorporated by reference herein in its entirety, to select genes having signatures that correlate with response signatures in accordance with the subject example.

Using SAM or any other microarray analysis, genes can be selected that most closely correlate with the derived response for a specific disease state that receives therapeutic benefit from a given therapy of interest. Permutation analysis can then used to estimate the false discovery rate (FDR). The resultant mean-centered gene expression vectors can then be clustered and visualized using known computer software (e.g., Cluster 3.0 and Java TreeView 1.03).

According to the present example, a gene classifier can be constructed to predict a specific disease state for which a given therapy of interest would be therapeutically effective in treating. In one embodiment, a gene classifier of the subject example is constructed using microarray data produced on a cDNA platform. In an embodiment, the classifier of the subject example is produced using SAM two-class gene selection and a support vector machine. In a related embodiment, the SAM procedure is empirically set to select enough genes to satisfy a set FDR. Such selected genes can then be used in a linear support vector machine to classify the samples as having poor or good response to the therapy of interest.

Leave-one-out cross-validation (LOOCY) can then be utilized to construct a classifier (e.g., neural network-based classifier) as well as to estimate the prediction accuracy of the classifier of the subject example. In one embodiment, the classification process includes both gene selection and SYM creation; therefore, both steps can be performed on a training set after the test example is removed. According to the subject example, samples can be classified as having a "therapeutically effective" or "poor" response to a given therapy of interest based on the strength of correlation between a measured profile and a given gene profile for a specific disease state.

By using the leave-one-out cross validation approach, the subject example provides a means for ranking the gene profiles for specific disease states that include a desired measured profiles. In one embodiment, the classifier of the subject example is prepared by (1) SAM gene selection using a t-test and (2) classification using a neural network. The classifier is prepared after a test sample is left out (from the LOOCY) to avoid bias from the gene selection step. Since the classification problem is a categorical decision, a t-test can be used for gene selection.

Once a gene set is selected, a feed-forward back-propagation neural network system (see Rumelhart et al., 1986, Cambridge, Mass.: MIT Press; and Fahlman, 1988, Proceedings of the Connectionist Models Summer School, Los Altos, Calif.: Morgan-Kaufmann; each of which is hereby incorporated by reference herein in its entirety) can be used. In one embodiment, a feed-forward back-propagation neural network with a single layer of 10 units is used.

The present example provides systems and methods for identifying tumor types for targeted clinical trials (e.g., Phase II clinical trials) based on molecular signatures of cancers. The method involves first the development of a measured molecular profile from a prospective clinical trial specifically designed to identify gene expression data produced on microarrays that predicts the response of a cell associated with a specific disease state ("response signature") to a given chemical agent or pharmaceutical drug. This prospectively derived profile is then used to scan a large, uniformly-derived molecular database for diseases/conditions (e.g., cancers) containing the same profile.

If a "match" is identified between the measured profile and a significant proportion of diseases/conditions (e.g., tumors of one type in the database), this would indicate a reasonable chance of the identified disease in responding to the chemical agent and/or pharmaceutical drug of interest. In one embodiment, an existing, effective pharmaceutical drug for a specific condition and/or disease is tested to identify gene expression data ("response signature") that predicts response of a patient having such condition and/or disease. Once the response signature is identified, it is compared against a gene expression database to identify any other conditions and/or diseases containing the same response signature parts. Those identified conditions and/or diseases that have a similar response signature could then be the target for a clinical trial (e.g., Phase II efficacy trial) of the therapy of interest with the anticipation that the drug would be effective in treating the newly identified conditions and/or diseases in accordance with the subject example. This would enable the researcher to bypass collection of Phase I data showing efficacy of the drug.

For example, 5-fluorouracil, which is known to be effective in the treatment of metastatic colon cancer, is tested to identify a gene expression signature ("response signature") that predicts response of metastatic colon cancer cells to 5-fluorouracil. The response signature is then compared against a gene expression database for tumors and any tumors containing the same response signature parts are identified.

One aspect of the present example provides systems and methods for identifying potentially responsive diseases and/or conditions to specific therapies of interest, where the therapy of interest has not yet been tested in clinical Phase II trials for the identified disease and/or condition. Such an approach is useful in providing prospective data with regard to therapy efficacy with regard to a specific disease and/or condition in lieu of conducting time consuming and expensive Phase I clinical trials. In addition, the systems and methods of the subject example are useful in providing data useful in designing Phase II clinical trials.

Further, the systems and methods of the subject example are cost effective not only in determining which types of patients and/or diseases/conditions best respond to a specific therapies of interest in a Phase II efficacy trial, but also allows for the identification of rare diseases/conditions for which the therapy of interest is therapeutically effective. Generally, rare diseases/conditions are not subjected to Phase I trials nor are commonly considered for Phase II trials; however, if responses were predicted in a particular type of rare disease/condition, as described in the subject invention, a Phase II trial might then be pursued.

6.2. Trial Matching

Figure 2A:
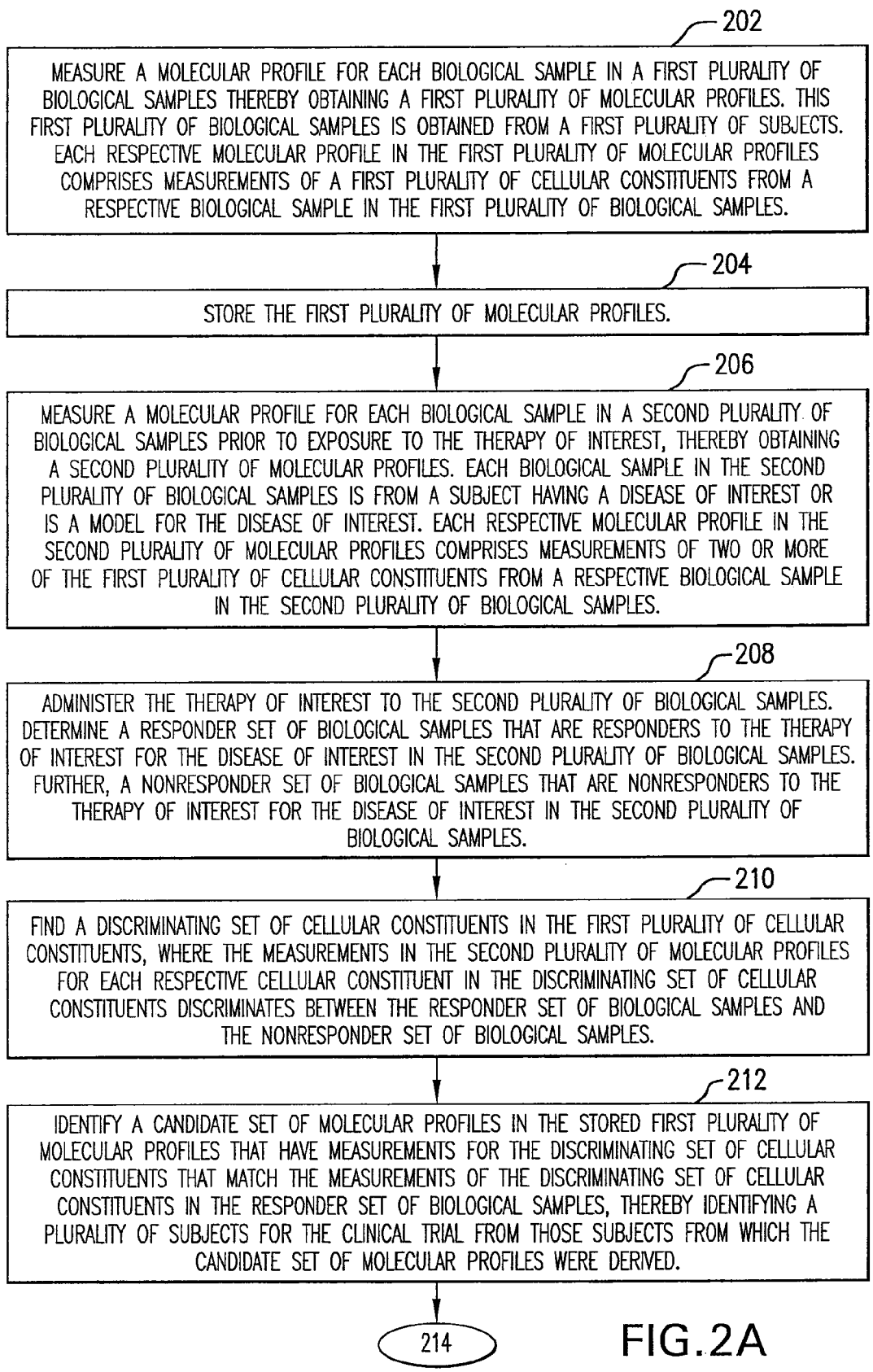
Figure 2B:
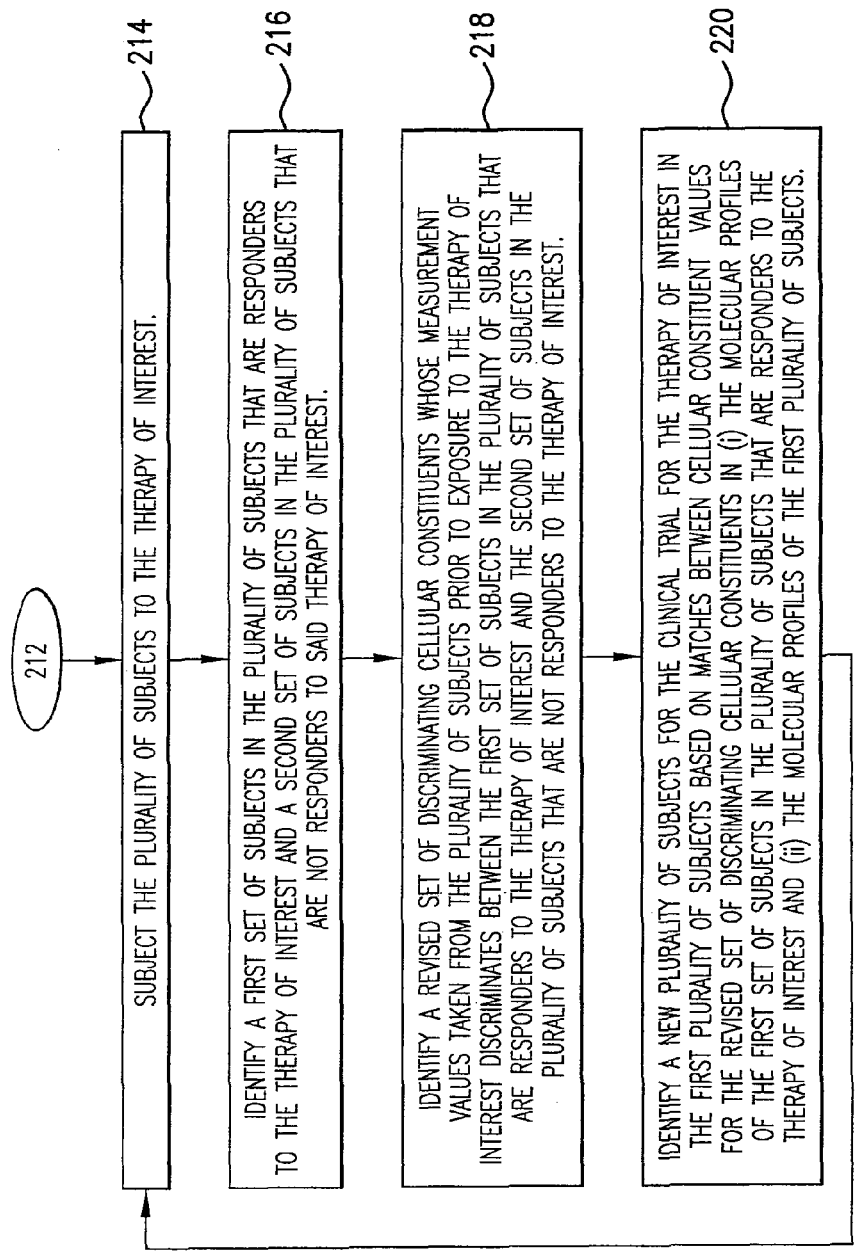
Figure 9B:
FIG. 9 illustrates representative screenshots of portions of a patient questionnaire, in accordance with an embodiment of the present invention.
Figure 9C:
Figure 9D:
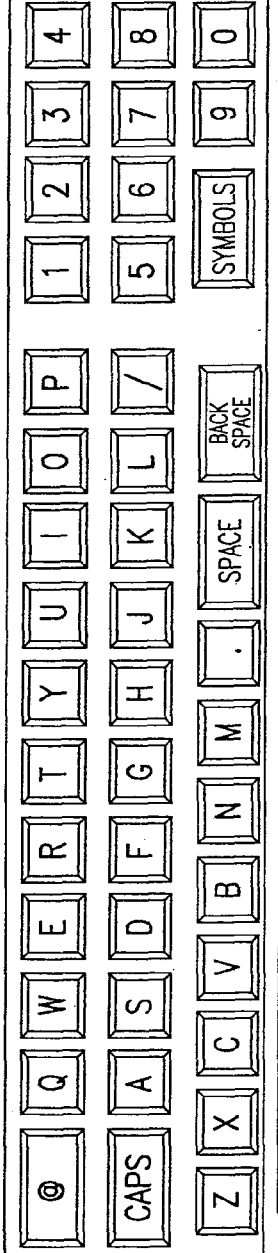
Figure 9E:

The following example provides an illustration of the methods disclosed above in conjunction with FIG. 2. The example serves to illustrate the methods and provide additional embodiments. However, the example in no way limits the methods described above in conjunction with FIG. 2.

Step 202. In this example, it is contemplated that there is one or more databases (e.g., patient database 42) that stores patient data for all patients that make use of a hospital, a hospital network, or any other medical institution. This database of patients is referred to above as a first plurality of patients. Thus, the patient database stores patient information for patients that have any number of different diseases In the present example, it is contemplated that a biological sample would be obtained from each of these patients. This patient sample could be, for example, obtained at the time that patients are first received, or soon thereafter. However, there is no limitation on when such a biological sample is received. One purpose for this biological sample is to obtain a molecular profile using the biological sample. A broad array of molecular profiles is contemplated. For instance, the molecular profile could be abundance data for several different genes that is obtained using a commercial nucleic acid microarray kit. As another example, the molecular profile could be abundance data for several different proteins that is obtained using a commercial protein array kit. Collectively, the molecular profiles obtained for the patients is referred to as a first plurality of molecular profiles. These molecular profiles may be obtained with purpose in addition to or other than for the purposes used in this example. For instance, the database of patients may include patients enrolled in various clinical trials, patients that have different diseases, and even patients that have deceased. In some embodiments, subjects that provide biological samples from which molecular profiles are obtained may have no diagnosed disease at all. These biological samples may be obtained, for example, in order to verify that the subjects have no disease.

Step 204. The plurality of molecular profiles that is measured in step 202 is stored so that they can be subsequently analyzed. Advantageously, though a given patient may have been enrolled for one type of disease, the molecular profile obtained from the patient may be used to help elucidate another unrelated disease. Note that the terms subject and patient are used interchangeably.

Step 206. In step 206 a molecular profile is measured for each biological sample from a second plurality of patients prior to exposure to a therapy of interest. It is quite possible that this second plurality of patients is simply a subset of the first plurality of patients described in step 202 above. However, the example is not so limited. The second plurality of subjects could be one or more cell lines that provide a good model for a particular disease. In any event, the goal in obtaining the second plurality of molecular profiles that is representative of a disease of interest (or is a model of the disease of interest). As has been noted, the second plurality of molecular profiles could be culled out of the molecular profiles obtained in step 202 (the first plurality). Moreover, the second plurality of molecular profiles can be added to the database that stores the first plurality of molecular profiles. In some embodiments, the second plurality of molecular profiles is not found in the database that stores the first plurality of molecular profiles. However, even in such instances, each respective molecular profile in the second plurality of molecular profiles comprises measurements of two or more of the first plurality of cellular constituents that were measured in the first plurality of molecular profiles. It should be noted that there is no requirement that the same cellular constituents be measured in every cellular constituent in the first plurality of molecular profiles. All that is required is that there is at least some cellular constituents that were measured in the second plurality of molecular profiles that were also measured in at least some of the first plurality of molecular profiles. Such overlap is needed between the first and second plurality of molecular profiles so that the second plurality of molecular profiles can serve to identify which of the first molecular profiles are from subjects that would be good candidates for a clinical trial and/or would likely to benefit from a give therapy.

Step 208. In step 208, a therapy of interest is administered to the second plurality of biological samples (or the subjects from which the biological samples were obtained). The purpose of such administration is to determine a responder set of biological samples that are responders to the therapy of interest for the disease of interest in the second plurality of biological samples. In the case where the therapy of interest is administered to subjects, the responder set of biological samples is in fact the subjects that responded to the therapy of interest. It should be noted that that step 208 contemplates both administering a therapy of interest directly to biological samples, administering a therapy of interest directly to biological samples, or both. In one example, the therapy of interest is a compound, it is administered to several different cell samples (e.g., cancerous cell lines), and the assay is for cell death. In another example, the therapy of interest is a compound, it is administered to subjects that have a disease, and the assay is to determine which subjects show improvement in symptoms associated with the disease and which do not. From this study, a nonresponder set of biological samples (or subjects) that are nonresponders to the therapy of interest for the disease of interest is identified and a responder set of biological samples (or subjects) that are responders to the therapy of interest for the disease of interest is identified.

Step 210. Step 208 served to find a set of responders and a set of nonresponders from within the second plurality of subjects. The set of responders and the set of nonresponders may be biological samples from individuals. Alternatively, the set of responders and the set of nonresponders may be individuals in the second plurality of individuals themselves. In either case, because each individual in the second plurality of individuals contributed a biological sample, it is possible to obtain cellular constituent abundance data from each member of the set of responders and the nonresponders. In step 208, a discriminating set of cellular constituents is identified. That is, the cellular constituents that discriminate between the responders and the nonresponders is identified. In some instances, a discriminating cellular constituent may be a SNP that is more prevalent in the responders than in the nonresponders or vice versa. In some instances, a discriminating cellular constituent may be one that is more abundant in the biological samples for the responders than in the biological samples in the nonresponders or vice versa. Any of a wide variety of statistical tests may be used to identify such discriminating cellular constituents. Section 5 above discloses a number of possible such techniques and others not identified in Section 5 may also be used. The net result of step 208 is a set of cellular constituents that discriminate between those subjects (or biological samples of such subjects) that respond to a therapy of interest and those that do not. Further, value ranges for such cellular constituents may also be determined. For instance, the measurement values for a discriminating cellular constituent in the responders versus nonresponders can be collected. In some embodiments, the end result of step 208 is the construction of a trained classifier (e.g., such as a trained neural network, a support vector machine, a logistic regression equation) that can be used to classify unknown subjects as either responders or nonresponders.

Step 212. In step 212, a candidate set of molecular profiles in the stored first plurality of molecular profiles that have measurements for the discriminating set of cellular constituents that match the measurements of the discriminating set of cellular constituents in the responder set of biological samples is identified. Thus, steps 202 through 212 serve to identify suitable subjects in a clinical trial. The second plurality of subjects used to identify the responders and the nonresponders is typically a small set of subjects or even just cell lines or other types of biological samples. Thus, the advantage of steps 202 through 212 is using a limited study to find subjects in a large patient pool (the first plurality of subjects) that are likely to benefit from a given therapy of interest. In some embodiments, step 210 creates a classifier that can be used to discriminate between responders and nonresponders in the first plurality of subjects. For instance, step 210 may result in a trained neural network. Cellular constituent abundance data from individual members of the first plurality of subjects may be used in this trained neural network to identify which subjects are suitable for a clinical trial and/or a therapy of interest and which subjects are not suitable for a clinical trial and/or a therapy of interest. In some embodiments, subjects in the first plurality of subjects that are suitable for a therapy of interest, based on analysis of the molecular profile of such subjects using the classifier or measurements of discriminating cellular constituents identified in step 210, are contacted so that they may benefit from the therapy of interest. Thus, steps 202-212 provide a way to not only identify subjects suitable for a clinical trial, it can also be used to identify subjects that would benefit from a therapy of interest. The discovery of a match between a therapy of interest and a subject in the first plurality of subjects (e.g., patient database 44) may occur at any time after the subject has been admitted to a medical program. Furthermore, the therapy of interest may be for a disease other than the one that cause the subject to be admitted to the program in the first instance.

6.3. Trial Matching

Steps 214-220 provide a feedback for iterative trial matching. In step 214, subjects identified in step 212 from the first population are subjected to the therapy of interest. It should be noted that a molecular profile from a biological sample is either measured or has previously been measured and stored prior to treatment with the therapy of interest. In some embodiments, a biological sample is taken from each subject treated in step 214 after treatment as well as a molecular profile obtained for each of these biological samples as well. Then, in step 216, subjects from step 214 that are responders and responders are identified. In step 218, a set of discriminating cellular constituents that discriminate between responders and nonresponders of step 216 are identified using statistical methods, pattern classification techniques or other methods. This set of discriminating cellular constituents is referred to as a revised set of discriminating cellular constituents. The revised set of discriminating cellular constituents is likely to have a substantial overlap with the set of discriminating cellular constituents identified in step 210. However, there is no requirement that there be any overlap (e.g., common cellular constituents) between the revised set of discriminating cellular constituents of step 218 and the set of discriminating cellular constituents of step 210. However, it is expected that the revised set of discriminating cellular constituents of step 218 and any classifier computed using measurement values for the discriminating cellular constituents of step 218 will provide an improved basis for identifying subjects in the first plurality of subjects (patient database 44) that are responders to the therapy of interest. In step 220, the measurement values for the revised set of discriminating cellular constituents from step 218 or the improved classifier derived therefrom is used to again poll the first plurality of subjects for subjects likely to respond to the therapy of interest. Steps 214 through 220 can be repeated any number of times in order to refine the revised set of discriminating cellular constituents and to refine the set of subjects that is likely to benefit from the therapy of interest. Such subjects can then be contacted for therapy.

7. REFERENCES CITED

Modifications

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of identifying a plurality of subjects for a clinical trial for a therapy of interest, the method comprising:

providing and storing a plurality of molecular profiles where each molecular profile is associated with a subject having a particular condition and is developed from a biological sample taken prior to treatment of any of the subjects using a therapy of interest;

providing and storing results of treating one or more of the subjects using the therapy of interest;

determining, after treatment of the one or more subjects, one or more responders of the one or more subjects to the therapy of interest where a responder is a subject that has a change in progression of the particular condition;

evaluating the molecular profiles of the one or more responders to determine a discriminating set of cellular constituents from among the cellular constituents in a respective molecular profile, wherein the discriminating set of cellular constituents distinguishes the molecular profiles of responders from the molecular profiles of subjects who were non-responders to the therapy of interest; and determining, by one or more processors, a candidate set of molecular profiles from the plurality of molecular profiles that were previously stored and not including the one or more subjects that were treated with the therapy of interest comprising, matching the discriminating set of cellular constituents against the molecular profiles of one or more non-treated subjects; and identifying a candidate set of subjects for a clinical trial whose molecular profiles match the discriminating set of cellular constituents without ex-vivo testing of each of the molecular profiles of respective subjects with the therapy of interest.

2. The method of claim 1, the method further comprising, prior to said determining a candidate set step, a step of measuring a molecular profile for each biological sample thereby obtaining the set of molecular profiles.

3. The method of claim 2, the method further comprising storing the set of molecular profiles.

4. The method of claim 1, the method further comprising, prior to said providing step, a step of:
measuring a molecular profile for each biological sample in a plurality of biological samples prior to exposure to said therapy of interest, thereby obtaining the set of molecular profiles, wherein each biological sample in the plurality of biological samples is from a subject having a disease of interest or is a model for said disease of interest and each respective molecular profile in the plurality of molecular profiles comprises measurements of two or more of a plurality of cellular constituents from a respective biological sample in the plurality of biological samples; and
determining a responder set of biological samples that are responders to said therapy of interest for the disease of interest in the plurality of biological samples and a non-responder set of biological samples that are nonresponders to the therapy of interest for the disease of interest in the plurality of biological samples.

5. The method of claim 4, wherein each biological sample in the plurality of biological samples is a cell line.

6. The method of claim 4, wherein each biological sample in the plurality of biological samples is obtained from a subject in a second plurality of subjects.

7. The method of claim 6, wherein each biological sample in the plurality of biological samples is a portion of a tumor.

8. The method of claim 1, the method further comprising steps of:
making a first observation of a clinical feature, other than a cellular constituent, in a subject in a plurality of subjects at a first time point; and
storing the first observation of the clinical feature with the molecular profile for the subject.

9. The method of claim 8, wherein the molecular profile for the subject is in the candidate set of molecular profiles and wherein the first observation is absence or presence of the clinical feature in the subject, the method further comprising:
removing the molecular profile from the candidate set when the clinical feature is absent from the subject; and
retaining the molecular profile in the candidate set when the clinical feature is present in the subject.

10. The method of claim 8, the method further comprising making a second observation of the clinical feature in the subject at a second time point; and
storing said second observation of the clinical feature with the molecular profile for the subject.

11. The method of claim 10, wherein the second time point is at least one day after the first time point.

12. The method of claim 10, wherein the second time point is at least one week after the first time point.

13. The method of claim 10, wherein the second time point is at least one month after the first time point.

14. The method of claim 10, wherein the second time point is at least one year after the first time point.

15. The method of claim 8, wherein the clinical feature is absence or presence of a disease in the subject.

16. The method of claim 15, wherein the disease is arthritis, asthma, an allergy, cancer, chronic fatigue syndrome, diabetes, epilepsy, heart disease, hemochromatosis, hepatitis B, hepatitis C, or osteoporosis.

17. The method of claim 15, wherein the disease is breast cancer, cervical cancer, colorectal cancer, lung cancer, oral cancer, ovarian cancer, prostate cancer, skin cancer, or testicular cancer.

18. The method of claim 8, wherein the clinical feature is ankle swelling, anorexia, dyspnoea, fatigue, high blood pressure, hypoxemia, lethargy, lymphopenia, nocturnal cough, nocturnal dyspnoea, obesity, orthopnoea, paroxysmal, a viral infection, reduced exercise tolerance, tachycardia, tachypnea, or wheeze.

19. The method of claim 1, wherein the method comprises obtaining each molecular profile for each biological sample using a microarray that comprises oligonucleotides representing more than five thousand cellular constituents.

20. The method of claim 1, wherein a cellular constituent in the discriminating set of cellular constituents is a nucleic acid or a protein.

21. The method of claim 1, wherein measurements for a cellular constituent in the set of discriminating set of cellular constituents discriminates with a p value of less than 0.05 as determined by a parametric or nonparametric test using measurements for a cellular constituent in a responder set of biological samples and measurements for the cellular constituent in a nonresponder set of biological samples.

22. The method of claim 21, wherein measurements are taken using a nonparametric test.

23. The method of claim 22, wherein the nonparametric test is a Chi-square test, a Phi coefficient, a Fisher exact test, or a Wilcoxon rank sum test.

24. The method of claim 21, wherein measurements are taken using a parametric test.

25. The method of claim 24, wherein the parametric test is analysis of variance or a t-test.

26. The method of claim 1, wherein the therapy of interest is exposure to a drug, exposure to radiation, exposure to radio-frequency ablation, or exposure to an siRNA.

27. The method of claim 1, wherein the plurality of subjects are human, bovine, porcine, canine, feline, ovine, equine, lapine, hamster, chicken, rat, mouse, chimpanzee, or baboon.

28. The method of claim 1, the method further comprising prior to the providing step:
obtaining patient information about a subject; and
storing the patient information about the subject with the molecular profile for the subject.

29. The method of claim 28, wherein the patient information is an address where the subject lives, next of kin contact information, a telephone number for the subject, an age of the subject, an allergy of the subject, a height of the subject, a weight of the subject, a race of the subject, insurance information for the subject, subject treatment history, a diagnosis of the subject, or family medical history for the subject.

30. The method of claim 29, wherein the patient information is entered directly onto a web-based questionnaire and wherein the storing step comprises completing the web-based questionnaire.

31. The method of claim 28, wherein the method further comprises:
removing a molecular profile from the candidate set when the patient information does not satisfy a selection criterion; and
retaining the molecular profile in the candidate set when the patient information satisfies the selection criterion.

32. The method of claim 31 wherein the selection criterion is a minimum age, a maximum age, a minimum weight, or a maximum weight.

33. The method of claim 1, the method further comprising:
identifying a revised set of discriminating cellular constituents whose measurement values taken from a plurality of subjects prior to exposure to the therapy of interest discriminates between responders to said therapy of interest and non-responders to said therapy of interest; and identifying a new plurality of subjects for the clinical trial for the therapy of interest based on matches between cellular constituent values for the revised set of discriminating cellular constituents in the stored set of the molecular profiles.

34. The method of claim 1, the method further comprising:
observing a progression of a disease in each subject in the subjects; and
storing said progression of said disease for each subject.

35. The method of claim 34, wherein the method further comprises:
removing the molecular profile of a subject from the candidate set when the progression of the disease in the subject does not satisfy a selection criterion; and
retaining the molecular profile of a subject in the candidate set when the progression of the disease in the subject satisfies the selection criterion.

36. The method of claim 35, wherein the selection criterion is a failure to respond to a therapy other than the therapy of interest.

37. The method of claim 35, wherein the selection criterion is responsiveness to a therapy other than the therapy of interest.

38. The method of claim 34, wherein the observing the progression of the disease comprises completing a web-based questionnaire.

39. The method of claim 1, the method further comprising:
administering to a subject the therapy of interest; and
storing a record of the therapy of interest in a record associated with the subject.

40. The method of claim 39, wherein the storing step comprises completing a web-based questionnaire.

41. The method of claim 1, the method further comprising:
obtaining a biological sample from a remote location.

42. The method of claim 41, wherein the obtaining step comprises entering patient data or clinical data associated with the biological sample, at the remote location, into a web-based questionnaire.

43. The method of claim 1, wherein each measurement of a cellular constituent in the discriminating set of cellular constituents in a molecular profile in the candidate set of molecular profiles is an indication of a presence or absence of one or more genetic markers.

44. The method of claim 43 wherein the cellular constituent is a nucleic acid and the one or more genetic markers are within the nucleic acid.

45. The method of claim 1, wherein each measurement of a respective cellular constituent in the discriminating set of cellular constituents in a molecular profile in the candidate set of molecular profiles is an abundance of the cellular constituent in a respective biological sample.

46. The method of claim 45 wherein the cellular constituent is nucleic acid or protein.

47. A computer program product for use in conjunction with a computer system, wherein the computer program product comprises a computer readable storage medium and a computer program mechanism embedded therein, the computer program mechanism for identifying a plurality of subjects for a clinical trial for a therapy of interest, the computer program mechanism comprising instructions for:
providing and storing a plurality of molecular profiles where each molecular profile is associated with a subject having a particular condition and is developed from a sample taken prior to treatment of any of the subjects using a therapy of interest and providing and storing results of using the therapy of interest on one or more of the subjects;
determining, after treatment of the one or more subjects, one or more responders to the therapy of interest where a responder is a subject that has a change in progression of the particular condition;
evaluating the molecular profiles of the one or more responders to determine a discriminating set of cellular constituents from among cellular constituents in a respective molecular profile, wherein the discriminating set of cellular constituents distinguishes the molecular profiles of responders from the molecular profiles of subjects who were non-responders to the therapy of interest; and
determining a candidate set of molecular profiles from the plurality of molecular profiles that were previously stored and not including the molecular profiles of the one more subjects with the therapy of interest comprising,
matching the discriminating set of cellular constituents against the molecular profiles of one or more non-treated subjects; and
identifying a candidate set of subjects for a clinical trial whose molecular profiles match the discriminating set of cellular constituents without ex-vivo testing of each of the molecular profiles of the subjects with the therapy of interest.

48. A computer comprising:
a central processing unit; and
a memory coupled to the central processing unit, the memory storing a module for identifying a plurality of subjects for a clinical trial for a therapy of interest, the module comprising instructions for:
providing and storing in the memory a plurality of molecular profiles where each molecular profile is associated with a subject having a particular condition and is developed from a sample taken prior to any of the subjects treatment using a therapy of interest and providing results of using the therapy of interest on one or more of the subjects;
determining, after treatment of the one or more subjects, one or more responders to the therapy of interest where a responder is a subject that has a change in progression of the particular condition;
evaluating the molecular profiles of the one or more responders to determine a discriminating set of cellular constituents from among cellular constituents in a respective molecular profile, wherein the discriminating set of cellular constituents distinguishes the molecular profiles of responders from the molecular profiles of subjects who were non-responders to the therapy of interest; and
determining a candidate set of molecular profiles in the plurality of molecular profiles and not including the one or more subjects that were treated with the therapy of interest comprising
matching the discriminating set of cellular constituents against the molecular profiles of one or more non-treated subjects; and
identifying a candidate set of subjects for a clinical trial whose molecular profiles match the discriminating set of cellular constituents without ex-vivo testing of each of the molecular profiles of respective subjects with the therapy of interest.

* * * * *